(12) United States Patent
Ueno et al.

(10) Patent No.: US 8,411,264 B2
(45) Date of Patent: Apr. 2, 2013

(54) METHOD AND APPARATUS FOR INSPECTING DEFECTS

(75) Inventors: Takeo Ueno, Kawasaki (JP); Hiroyuki Nakano, Mito (JP); Yasuhiro Yoshitake, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 238 days.

(21) Appl. No.: 12/504,972

(22) Filed: Jul. 17, 2009

(65) Prior Publication Data

US 2010/0014083 A1    Jan. 21, 2010

(30) Foreign Application Priority Data

Jul. 18, 2008  (JP) .................................. 2008-186651

(51) Int. Cl.
*G01N 21/00* (2006.01)

(52) U.S. Cl. ............... 356/237.5; 356/237.1; 356/237.4; 356/237.6

(58) Field of Classification Search ..... 356/237.2–237.5
See application file for complete search history.

(56) References Cited

U.S. PATENT DOCUMENTS

| | | | | |
|---|---|---|---|---|
| 6,404,498 | B1 * | 6/2002 | Maeda et al. ................. | 356/394 |
| 7,061,600 | B2 * | 6/2006 | Maeda et al. ................. | 356/237.2 |
| 7,710,557 | B2 * | 5/2010 | Oshima et al. ................ | 356/237.5 |
| 2006/0139629 | A1 * | 6/2006 | Ohshima et al. .............. | 356/237.2 |
| 2007/0070337 | A1 * | 3/2007 | Ohshima et al. .............. | 356/237.3 |
| 2007/0177136 | A1 * | 8/2007 | Nakano et al. ............... | 356/237.2 |
| 2009/0059216 | A1 * | 3/2009 | Shibata et al. ............... | 356/237.4 |
| 2009/0141269 | A1 | 6/2009 | Uto et al. | |
| 2009/0213366 | A1 | 8/2009 | Nakano et al. | |
| 2010/0182602 | A1 | 7/2010 | Urano et al. | |

FOREIGN PATENT DOCUMENTS

| | | |
|---|---|---|
| JP | 08-138198 | 5/1997 |
| JP | 11-271231 | 10/1999 |
| JP | 2002-139428 A | 5/2002 |
| JP | 2002-228606 A | 8/2002 |
| JP | 2003-083907 | 3/2003 |
| JP | 2003-098113 | 4/2003 |
| JP | 2003-271927 | 9/2003 |
| JP | 2007-33433 A | 2/2007 |
| JP | 2007-232555 A | 9/2007 |
| JP | 2008-20374 A | 1/2008 |

* cited by examiner

*Primary Examiner* — Tarifur Chowdhury
*Assistant Examiner* — Isiaka Akanbi
(74) *Attorney, Agent, or Firm* — Antonelli, Terry, Stout & Kraus, LLP.

(57) ABSTRACT

An apparatus for inspecting a substrate surface is provided, which includes illumination optics for irradiating the substrate surface linearly with rectilinearly polarized light from an oblique direction, detection optics for acquiring images of the substrate surface, each of the images being formed by the light scattered from the light-irradiated substrate surface, and means for comparing an image selected as an inspection image from the plurality of substrate surface images that the detection optics has acquired to detect defects, and another image selected from the plural images of the substrate surface as a reference image different from the inspection image; the illumination optics being formed with polarization control means for controlling a polarizing direction of the light according to a particular scanning direction of the substrate or a direction orthogonal to the scanning direction.

19 Claims, 18 Drawing Sheets

A VIEWING POINT
RECTILINEARLY POLARIZED LIGHT
ENTERS AT AZIMUTH ANGLE "$\alpha$"

$$\alpha = \tan^{-1}\left(\frac{\tan\phi}{\cos\theta}\right)$$

B VIEWING POINT
RECTILINEARLY POLARIZED LIGHT
ENTERS AT AZIMUTH ANGLE "$-\alpha$"

$$-\alpha = \tan^{-1}\left(-\frac{\tan\phi}{\cos\theta}\right)$$

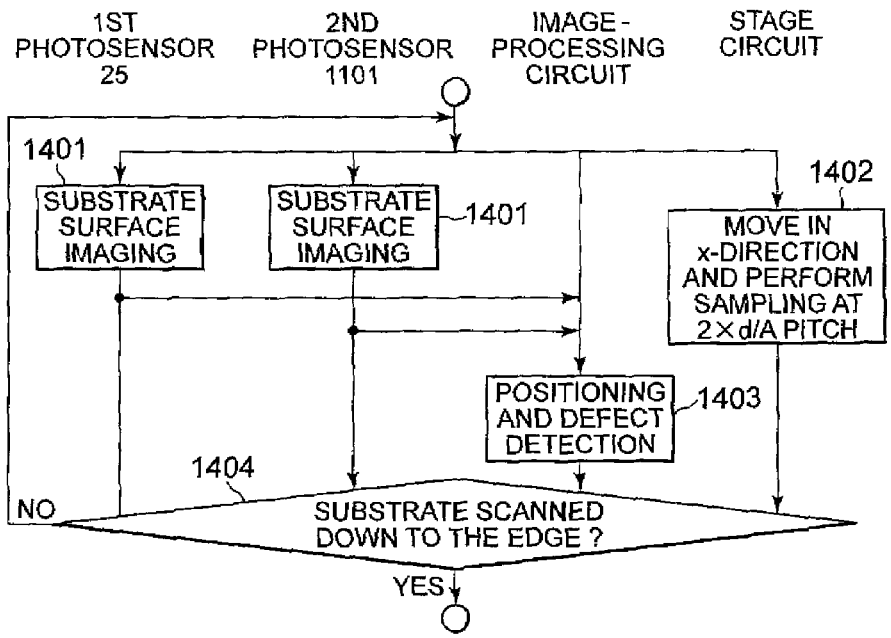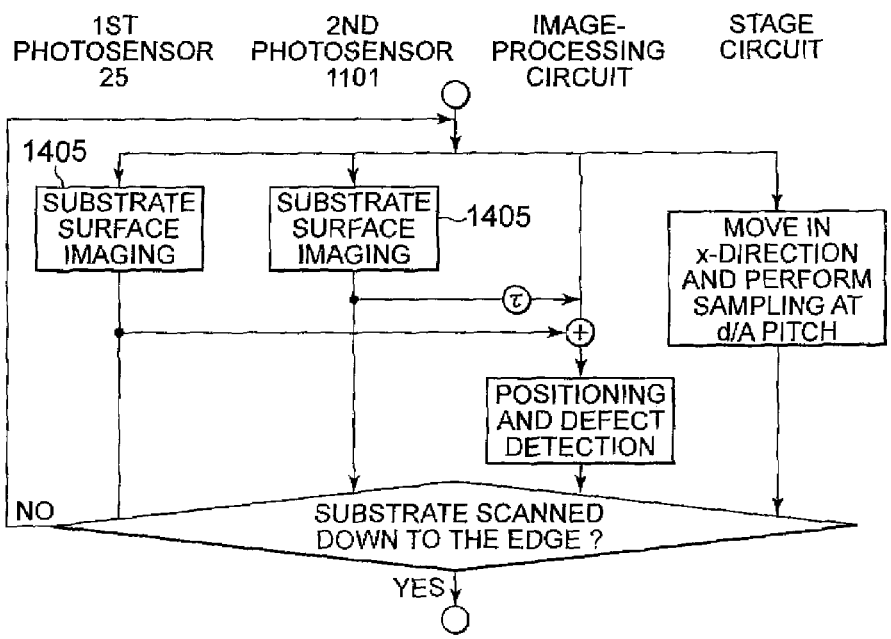

METHOD AND APPARATUS FOR INSPECTING DEFECTS

BACKGROUND OF THE INVENTION

The present invention relates generally to defect inspection methods and apparatus for detecting microstructured pattern defects, contamination, and the like, by comparing an optically acquired image of an object to be inspected, and a reference image. More particularly, the invention relates to a method and apparatus for inspecting defects in a semiconductor device, a photomask, a liquid crystal, and other objects, in optical technique.

During the manufacture of a semiconductor device, a substrate (wafer) on which the semiconductor device is to be formed undergoes processing through hundreds of manufacturing process steps to become a product. In these process steps, for example, if any kinds of contamination sticking to the surface of the substrate (wafer) are found or if the non-uniformity of pattern formation between processes occurs, these undesirable events will cause pattern defects, rendering the semiconductor device defective. In addition, with the progress of pattern microstructuring, defect inspection systems for semiconductor devices are more strongly required to not only detect defects and contamination of a finer structure, but also detect the defects of interest (DOIs). At the same time, needs for classifying non-intended defects separately from various DOIs are also increasing. In order to meet these requirements and needs, various types of defect inspection apparatus including a plurality of detection optics and image-processing circuits (detection heads) to increase the number of defect species detectable using detection signals of the detection optics, and to improve defect detection performance, have come to be developed, manufactured, and sold in recent years, and are being applied to semiconductor-manufacturing equipment.

Defect inspection apparatus for semiconductor devices is used, for example, to inspect the surfaces of substrates after each process and detect any pattern defects and contamination that may have occurred during processes such as lithography, film deposition, or etching. The inspection apparatus is also used to issue a cleaning execution command for an apparatus conducting the process, and to early detect the occurrence of defectives due to the possible movement of critically defective substrates to the next or subsequent process sites.

The substrate on which the semiconductor device provided with required processing in the previous process has been semi-formed is loaded into the inspection apparatus, and the surface of the substrate (wafer) with the semi-formed semiconductor device is imaged. Defect discriminations based on acquired images are performed using such a threshold-based defect signal discrimination process as described in Patent Document 1 (JP-A-2003-83907), Patent Document 2 (JP-A-2003-98113, or Patent Document 3 (JP-A-2003-271927), and information such as the number of defects present on the substrate is output.

If the number of actually detected defects, Nt, is smaller than the preset defect detection threshold value Nc, the substrate will be directly moved to the next process site intact. Conversely if the number of detected defects, Nt, is larger than the defect detection threshold value Nc, a command for cleaning the previous process apparatus will be issued before the substrate is judged for reproducibility. The substrate, if judged to be reproducible, will be cleaned in a cleaning process and then subjected to the defect inspection process once again before being moved to the next process site.

As shown in FIG. 4, dies 401 and 401' of the same pattern are arranged regularly on the semiconductor substrate to be inspected. Defects are discriminated by comparing images of these adjacent dies present at the same coordinate positions thereof in the die regions. In this case, defect-inspecting illumination optics based on conventional darkfield optics have employed s-polarized, p-polarized, and/or circularly polarized illumination light. One reason for this is that when only contamination present on a silicon substrate is to be inspected, the detection performance required can be obtained under both s-polarized illumination and p-polarized illumination. Another reason is that for contamination present on oxide films and other transparent films, the effects of changes in the amount of scattered light due to changes in film thickness can be reduced by using circularly polarized illumination light. Briefly, s-polarized illumination, p-polarized illumination, and/or circularly polarized illumination have sufficed to improve the detection performance of the optics with respect to the contamination existing on the substrate or films. Even for a wafer with patterns, if the pattern pitch is much the same as the wavelength of the light, defects between the patterns have been detectable without a problem.

SUMMARY OF THE INVENTION

There have been the problems, however, that if the wafer includes patterns and the pattern pitch is shorter than the wavelength of the light, since the semiconductor patterns themselves will have polarizing characteristics, the polarization characteristics of the light diffracted from the patterns will also change and defect detection performance will decrease as a result. For a wafer with vertically long patterns, in particular, short-circuiting defects at the bottoms of the patterns have been difficult to detect with high sensitivity.

The present invention for solving the above problems provides a defect inspection method and defect inspection apparatus capable of achieving highly accurate defect detection by controlling polarization of illumination light according to scattered-light characteristics of defects to be detected.

Of all aspects of the present invention that are disclosed in this application, only typical ones are outlined below.

(1) An apparatus for inspecting a substrate surface, the apparatus comprises: illumination optics for irradiating the substrate surface linearly with rectilinearly polarized light from an oblique direction; detection optics for acquiring images based on beams of light scattered from the substrate surface irradiated with the polarized light; and means for comparing an image selected as an inspection image from the plurality of substrate surface images that the detection optics has acquired, and another image selected from the plurality of substrate surface images as a reference image different from the inspection image to detect a defect; wherein the illumination optics includes polarization control means for controlling a polarizing direction of the light according to a particular scanning direction of the substrate or a direction orthogonal to the scanning direction.

(2) The inspection apparatus according to above item (1), wherein the illumination optics is constructed such that the substrate is irradiated with the light obliquely at an azimuth angle of 15 to 75 degrees with respect to the scanning direction of the substrate.

(3) An apparatus for inspecting a substrate surface, the apparatus comprises: first illumination optics for irradiating the substrate surface linearly with a rectilinearly polarized beam of light from a first oblique direction; second illumination optics for irradiating the substrate surface linearly with another rectilinearly polarized beam of light from a second oblique direction; detection optics for acquiring images based on the beams of light scattered from the substrate surface irradiated with the beams from the first and second illumination optics; and means for comparing an image selected as an inspection image from the plurality of substrate surface images that the detection optics has acquired, and another image selected from the plurality of substrate surface images as a reference image different from the inspection image to detect a defect; wherein the first illumination optics and the second illumination optics each includes polarization control means for controlling a polarizing direction of the light according to a particular scanning direction of the substrate or a direction orthogonal to the scanning direction.

(4) The inspection apparatus according to above item (3), wherein: the direction in which the light is polarized on the substrate surface by the first illumination optics is adjusted to be substantially the same as the direction in which the light is polarized on the substrate surface by the second illumination optics; and in the detection optics, scattered light whose polarized states are substantially the same are detected in the lump by a plurality of photosensors arranged appropriately to gear up to illumination regions of the first illumination optics and the second illumination optics.

(5) The inspection apparatus according to above item (3), wherein: the direction in which the light is polarized on the substrate surface by the first illumination optics is adjusted to be substantially orthogonal to the direction in which the light is polarized on the substrate surface by the second illumination optics; and in the detection optics, scattered light whose polarized states differ from each other are detected in the lump by a plurality of photosensors arranged to correspond to illumination regions of the first illumination optics and the second illumination optics.

These and other objects, features and advantages of the present invention will be apparent from the following more particular description of preferred embodiments of the invention, as illustrated in the accompanying drawings.

BRIEF DESCRIPTION OF THE DRAWINGS

FIG. 14A is a first operation flow focusing on stage operation of the inspection apparatus according to the first embodiment of the present invention;

FIG. 14B is a second operation flow focusing on the stage operation of the inspection apparatus according to the first embodiment of the present invention;

DESCRIPTION OF THE EMBODIMENTS

Hereunder, embodiments of the present invention will be described.

Figure 1:
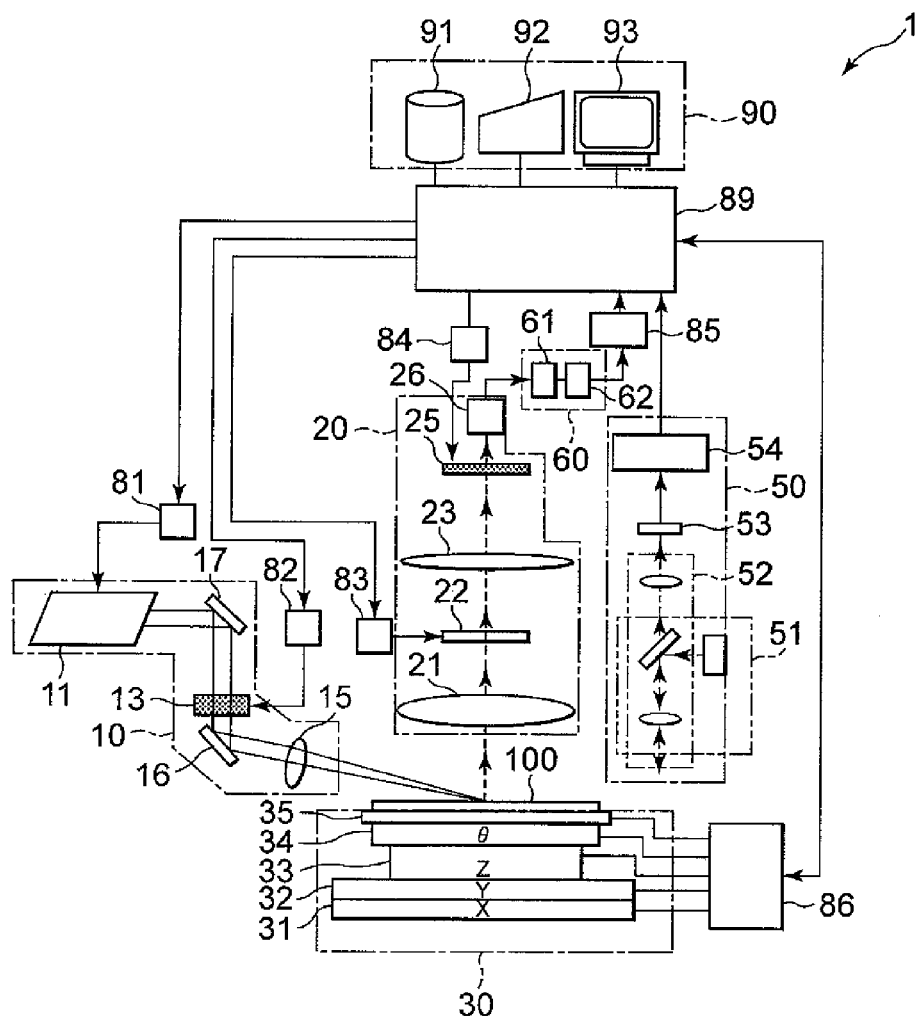
FIG. 1 is a diagram showing a first embodiment of an inspection apparatus according to the present invention.

A first embodiment of an inspection apparatus according to the present invention is described below with reference to FIG. 1, a block diagram of the inspection apparatus. The inspection apparatus 1 includes, as appropriate, illumination optics 10 for irradiating the surface of a substrate (wafer) 100 after shaping a beam of light emitted from a light source 11, detection optics 20 for detecting/imaging the light scattered from the substrate 100, a substrate conveying circuit 30 for conveying the substrate 100, a focal measuring circuit 50 for automatic focusing, an image-processing circuit 60 for processing the scattered light signal/image detected by the detection optics 20, a control and processing circuit for controlling the entire apparatus, and an interface circuit 90.

The illumination optics 10 is constructed using, as appropriate, the laser light source 11, reflecting mirrors 16 and 17 that guide in a required direction the light emitted from the laser light source 11, a polarization control unit 13 that controls a polarized state of the light, and a condensing lens 15 that shapes the light into a required beam form.

For detection of very small defects present near the wafer surface, a light source that generates short-wavelength ultraviolet or vacuum ultraviolet laser beams and provides a high output energy of at least 1 W is used as the laser light source 11. A light source that generates visible or infrared laser beams is used for detection of defects present inside the wafer.

A region on the wafer surface irradiated with the laser light takes a long shape in a certain direction and short in a direction vertical thereto, by using a cylindrical lens as the condensing lens 15. Alternately, using anamorphic optics (composed of a plurality of prisms) to change a diameter of the beam with respect only to one direction in a plane vertical to an optical axis, and then using a circular lens, will allow illumination of a region taking a shape long in a certain direction on the wafer and short in a direction vertical thereto. The anamorphic optics is effective for making the optical axis easily adjustable.

Figure 3:
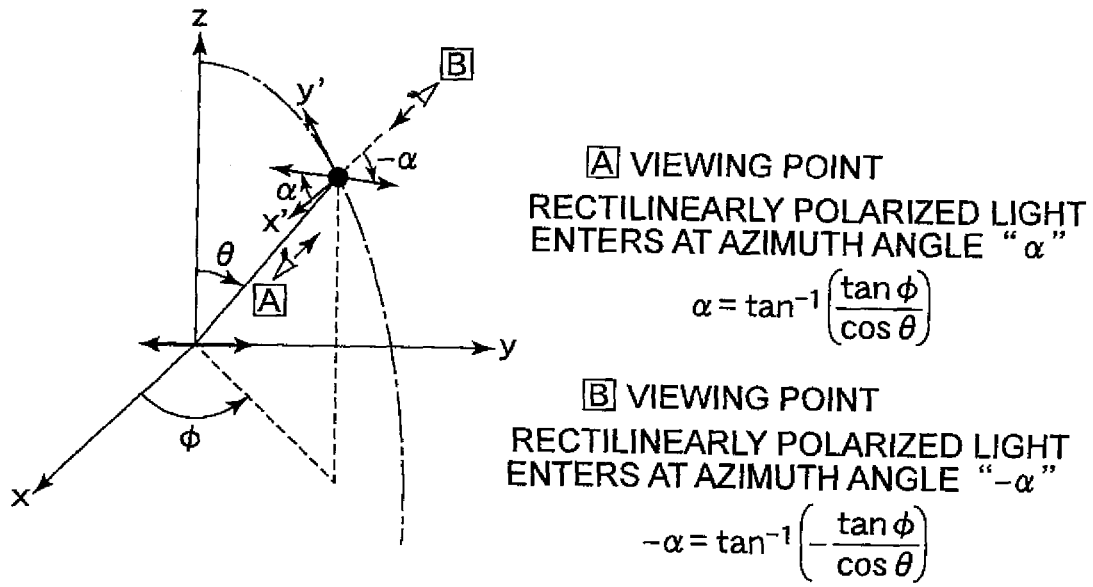
FIG. 3 is an illustrative diagram of a method for adjusting a polarizing direction by means of illumination optics.
Figure 4:
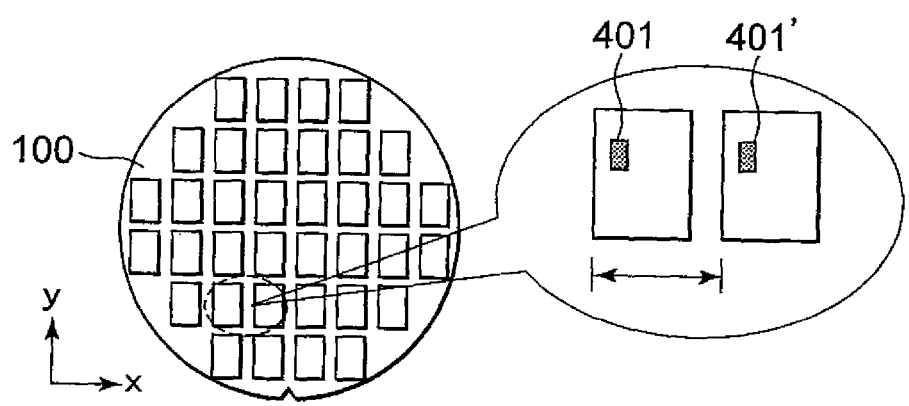
FIG. 4 is a diagram that shows layout of chips on a substrate to be inspected, and a scanning direction of the substrate.

In the present embodiment, a polarizing direction of the light emitted from the light source 11 is controlled by the polarization control unit 13 so that rectilinear polarization is achieved and so that the light is polarized in an x-direction or a y-direction on the substrate. The polarization-controlled light is further changed into a shape of a sheet-like beam using the cylindrical lens as the lens 15, and then the surface of the substrate 100 is irradiated with this beam. The polarized state of the illumination light is controlled by the polarization control unit 13 to ensure that as shown in FIG. 3, a rotational angle from the illumination axis for polarized illumination becomes equal to a rotational angle calculated from an azimuth angle and elevation angle of the illumination light.

Figure 2A:
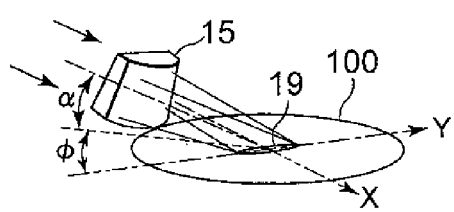
FIG. 2A is a first illustrative diagram of linear illumination by the inspection apparatus according to the first embodiment of the present invention.
Figure 2B:
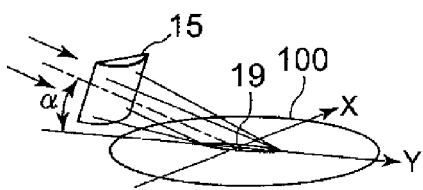
FIG. 2B is a second illustrative diagram of linear illumination by the inspection apparatus according to the first embodiment of the present invention.

In the present embodiment, if, as shown in FIG. 2, the wafer is scanned in the x-axis direction, the region 19 illuminated in sheet-shaped form on the wafer takes a long shape in a direction orthogonal to the scanning direction of the wafer, that is, substantially in the y-axis direction. At this time, a relationship in position between the wafer region 19 irradiated with the illumination light, and a photosensor 25 in FIG. 1, is made conjugate through the detection optics 20. Simultaneous detection of the entire sheet-shaped region by the photosensor 25 allows a surface image of the wafer 100 to be acquired at high speed. In addition, as described later herein, in the present embodiment, the azimuth angle $\phi$ and elevation angle $\alpha$ of the illumination light are each used at several selectable levels. More specifically, the azimuth angle $\phi$ of the illumination light is used, as shown in FIG. 2A, in a range of nearly $\phi=15°–75°$ (desirably, $\phi$ is nearly equal to 45°), rather than as $\phi$ is nearly equal to 0° shown in FIG. 2B.

The detection optics 20 includes, as appropriate, an objective lens 21, a spatial filter 22, an image-forming lens 23, and an analog/digital (A/D) conversion unit 26, in addition to the photosensor 25. A line sensor or a TDI sensor is used, as appropriate, as the photosensor 25 in the detection optics. In this case, the so-called TDI operation in which a product between a feed rate of a stage and a line rate of the TDI sensor matches a product between a line spacing and a magnification of the optics, is required and to achieve this, a mechanism not shown is required that establishes synchronization between a control circuit of the stage and the TDI sensor.

In addition, a polarizing filter or an attenuator may be inserted between the image-forming lens 23 and the photosensor 25. If the polarizing filter is inserted, polarized components of the scattered light from the sample surface detected can be arbitrarily selected by controlling a direction of the polarizing filter. If the attenuator is inserted, since the amount of light entering the photosensor 25 can be reduced without changing the illumination light in luminous intensity, an output current of the photosensor 25 can be prevented from saturating.

An image of the irradiated region 19 shown in FIG. 2 is formed on the photosensor 25 by the above image-forming optics. An output from the photosensor 25 is converted into a digital signal by the A/D conversion unit 26, from which the digital signal is then input to the image-processing circuit 60.

The substrate conveying circuit 30 includes, as appropriate, an X-stage 31, a Y-stage 32, a Z-stage 33, a θ-stage 34, and a substrate chuck 35 in which the substrate is mounted.

The focal measuring circuit 50 includes, as appropriate, illumination optics 51 for focal measurement, detection optics 52 for focal measurement, a photosensor 53, and a focus error calculation unit 54. In the focal measuring circuit 50, light formed by scattering of the light with which the wafer has been irradiated by the illumination optics 51 is detected by the detection optics 52 and the photosensor 53, and then based upon the detected signal, an average of focus error data measurements obtained over a time long enough to allow reduction of noise components is calculated in a range not exceeding a period at which the focus error calculation unit 54 calculates position error information on a differential between images of adjacent dies. Use of the calculated focus error data allows correction for any deviations in positional relationship between internal coordinates of a measuring field of view and on-wafer coordinates.

The image-processing circuit 60 includes, as appropriate, an adjacent die-to-die image position error information calculation unit 61 and a data processing unit 62 for discriminating and detecting defects using the die-to-die differential image.

The control and processing circuit includes, as appropriate, an illumination light source control unit 81 for controlling the laser light source 11, a unit controller 82 for controlling the polarization control unit 13, a spatial filter control unit 83 for controlling the spatial filter 22, a sensor control unit 84 for controlling the photosensor 25, a defect information-processing unit 85 for merging and classifying the defect information output from the image-processing circuit 60, a conveying circuit control unit 86 for controlling the substrate conveying circuit 30, and a control unit 89 for undertaking total control of these control/processing circuit elements.

The interface circuit 90 includes, as appropriate, a data storage section 91 for storing the defect information that the control and processing circuit has processed and output, an input section 92 for executing inspection parameter setting and control process information input, and a display section 93 for displaying the defect information and control process information.

Next, a relationship between an illumination azimuth angle and a distribution of pattern-diffracted light on a Fourier transform plane is described below with reference to FIGS. 5A to 5D.

In general, a large majority of patterns on a wafer are occupied by the patterns extending long in the x-axis direction and arranged in the y-axis direction, and the patterns extending long in the y-axis direction and arranged in the x-axis direction. Accordingly, the distribution 2173 of the pattern-diffracted light on the Fourier transform plane during darkfield illumination includes a crisscross high-intensity section extending long in both x-axis and y-axis directions, with a center at that position in a direct-reflection direction 2172 which is equivalent to regular-reflected light relative to the illumination light 2171 with which the above region is irradiated.

Figure 5A:
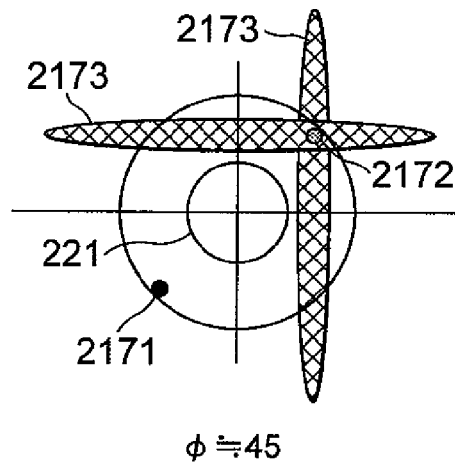
FIG. 5A is a diagram showing schematically a relationship in position, established between directly reflected light, pattern-diffracted light, and a detection optics aperture on a Fourier transform plane of inspection optics, at an illumination azimuth angle of nearly 45 degrees.
Figure 5B:
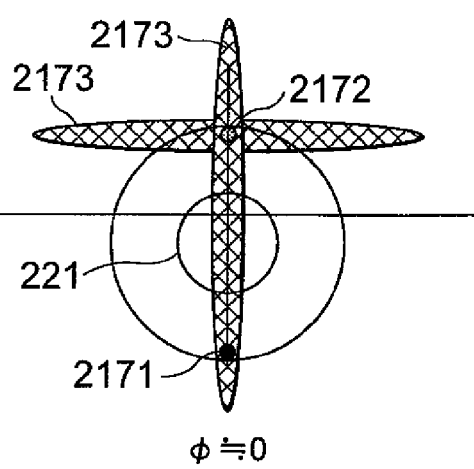
FIG. 5B is a diagram showing schematically a relationship in position, established between directly reflected light, pattern-diffracted light, and the detection optics aperture on the Fourier transform plane of the inspection optics, at an illumination azimuth angle of nearly 0 degrees.
Figure 5C:
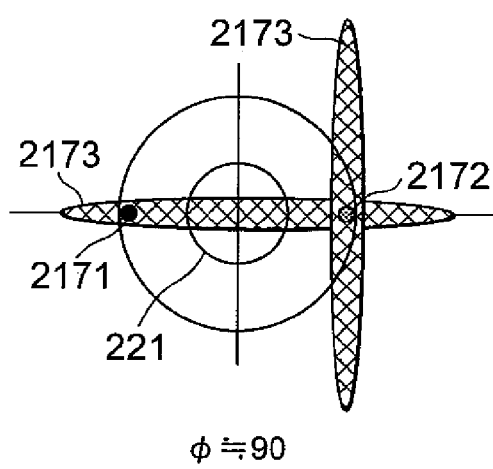
FIG. 5C is a diagram showing schematically a relationship in position, established between directly reflected light, pattern-diffracted light, and the detection optics aperture on the Fourier transform plane of the inspection optics, at an illumination azimuth angle of nearly 90 degrees.

For example, if the illumination azimuth angle $\phi$ is nearly equal to 0° or $\phi$ is nearly equal to 90°, the light diffracted from the patterns will enter an aperture 221 of the objective lens 21 of the detection optics 20 at both of those angles, as shown in FIGS. 5B and 5C, respectively. In general, the amount of light scattered from a defect is very small, compared with that of light diffracted from a pattern. At the above illumination azimuths, therefore, defects become difficult to detect. In this case, although the diffracted light from the pattern can be suppressed by disposing a spatial filter or the like on the Fourier transform plane, the problem of a decrease in sensitivity arises since the scattered light is also blocked simultaneously with the suppression of the diffracted light.

Figure 5D:
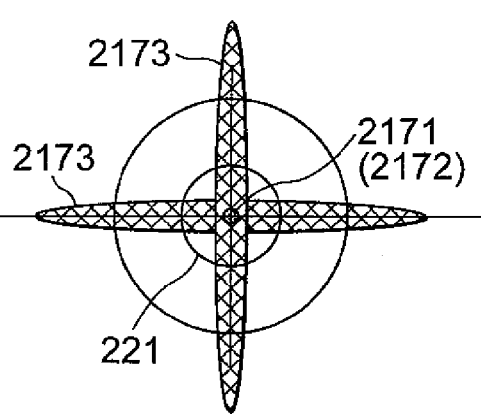
FIG. 5D is a diagram showing schematically a relationship in position, established between directly reflected light, pattern-diffracted light, and the detection optics aperture on the Fourier transform plane of the inspection optics, under episcopic illumination.

In contrast to the above, if the illumination azimuth angle $\phi$ is nearly equal to 45°, automatic detection only of the high-intensity section of the pattern-diffracted light can be omitted as shown in FIG. 5A, by selecting an appropriate size for the detection aperture 221. Accordingly, defect detection sensitivity can be improved by blocking only specific pattern-diffracted light with a spatial filter. On the distribution of the pattern-diffracted light during episcopic illumination, the diffracted light from the pattern spreads over a large portion of the aperture 221 of the objective lens 21, as shown in FIG. 5D, so that it is more difficult to observe only the defect without detecting the pattern.

Figures 6A, 6B, 6C, 6D:
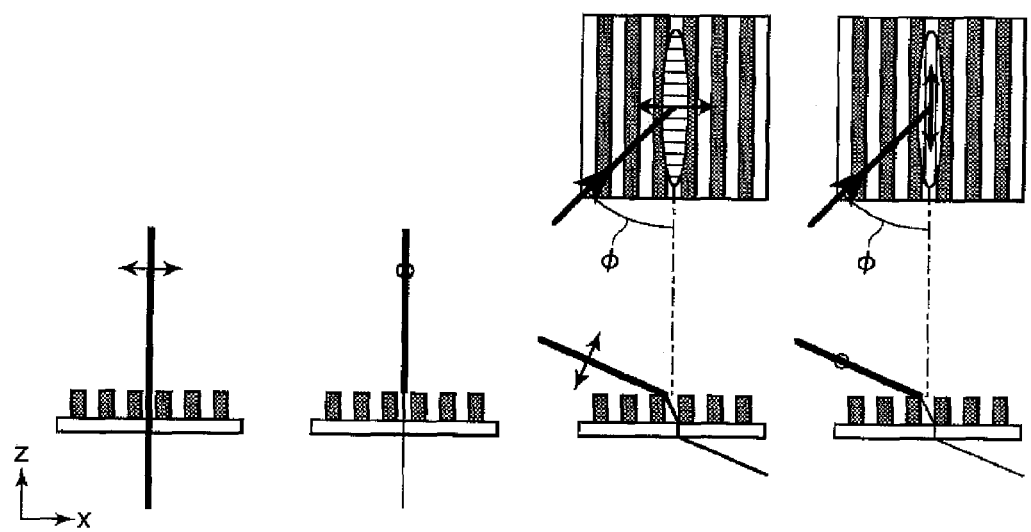
FIG. 6A is a diagram showing schematically a transmittance of light with which metallic iterative patterns created on a glass substrate are irradiated from an episcopic direction, the light being inclusive of components polarized in the same direction as an array direction of the patterns.
FIG. 6B is a diagram showing schematically a transmittance of light with which the metallic iterative patterns created on the glass substrate are irradiated from another episcopic direction, the light being inclusive of the components polarized in the same direction as a lengthwise direction of the patterns.
FIG. 6C is a diagram showing schematically a transmittance of light with which the metallic iterative patterns created on the glass substrate are irradiated from an oblique direction, the light being inclusive of the components polarized in the same direction as the array direction of the patterns.
FIG. 6D is a diagram showing schematically a transmittance of light with which the metallic iterative patterns created on the glass substrate are irradiated from another oblique direction, the light being inclusive of the components polarized in the same direction as the lengthwise direction of the patterns.
Figures 7A, 7B, 7C, 7D:
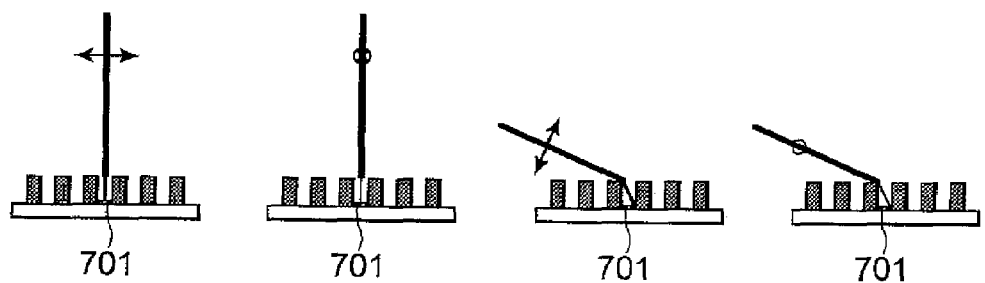
FIG. 7A is a diagram showing schematically a ratio at which illumination light reaches a short-circuiting defect formed at the bottom of the iteratively patterned metal section, between the patterns, the defect being irradiated from an episcopic direction with the above illumination light inclusive of components polarized in the same direction as the array direction of the patterns.
FIG. 7B is a diagram showing schematically a ratio at which illumination light reaches the short-circuiting defect formed at the bottom of the iteratively patterned metal section, between the patterns, the defect being irradiated from an episcopic direction with the above illumination light inclusive of components polarized in the same direction as a lengthwise direction of the patterns.
FIG. 7C is a diagram showing schematically a ratio at which illumination light reaches the short-circuiting defect formed at the bottom of the iteratively patterned metal section, between the patterns, the defect being irradiated from an oblique direction with the above illumination light inclusive of components polarized in the same direction as the array direction of the patterns.
FIG. 7D is a diagram showing schematically a ratio at which illumination light reaches the short-circuiting defect formed at the bottom of the iteratively patterned metal section, between the patterns, the defect being irradiated from an oblique direction with the above illumination light inclusive of components polarized in the same direction as the lengthwise direction of the patterns.

FIGS. 6A to 6D each show schematically a transmittance of illumination light with which metallic linear iterative patterns whose pitch is shorter than the wavelength of the light formed on the substrate of a material (e.g., glass) transparent to the illumination light are irradiated from an episcopic direction (FIG. 6A) or an oblique direction (FIG. 6C) or from another episcopic direction (FIG. 6B) or another oblique direction (FIG. 6D). In the former two cases, the light includes the components polarized in the same direction as an array direction of the patterns, and in the latter two cases, the light includes the components polarized in the same direction as a lengthwise direction of the patterns. As shown in FIGS. 6A-6D, the transmittance of the illumination light (FIG. 6A, 6C) including the components polarized in the same direction as the array direction of the patterns is about 10 to 100 times as large as the transmittance of the illumination light (FIG. 6B, 6D) including the components polarized in the same direction as the lengthwise direction of the patterns. This feature holds true for not only vertical illumination relative to the filter, but also oblique illumination.

The light scattered from a short-circuiting defect 701 present at the bottom of a pattern is studied below using FIGS. 7A to 7D, under the same conditions as those of FIGS. 6A to 6D. Episcopic illumination is more efficient for making the illumination light reach the short-circuiting defect 701. As described previously as per FIGS. 5A-5D, however, in consideration of avoiding pattern-diffracted light detection in provision against decreases in defect detection sensitivity due to the pattern-diffracted light, illumination at an oblique illumination azimuth angle slightly offset from 0° or 90° (e.g., φ=15° to 75°, desirably, φ is nearly equal to 45°) is suitable for defect detection.

With the above taken into account, oblique illumination at which φ is nearly equal to 45° azimuth angle (FIG. 7C) to the scanning direction of the wafer with the light polarized in the array direction of the patterns, near the wafer surface, provides the highest detection sensitivity for the defect 701. For this reason, φ=45° is taken as an example in the description of the present embodiment.

Next, operation flow of the inspection apparatus according to the present embodiment is described below with reference to FIGS. 8 and 9.

Figure 8:
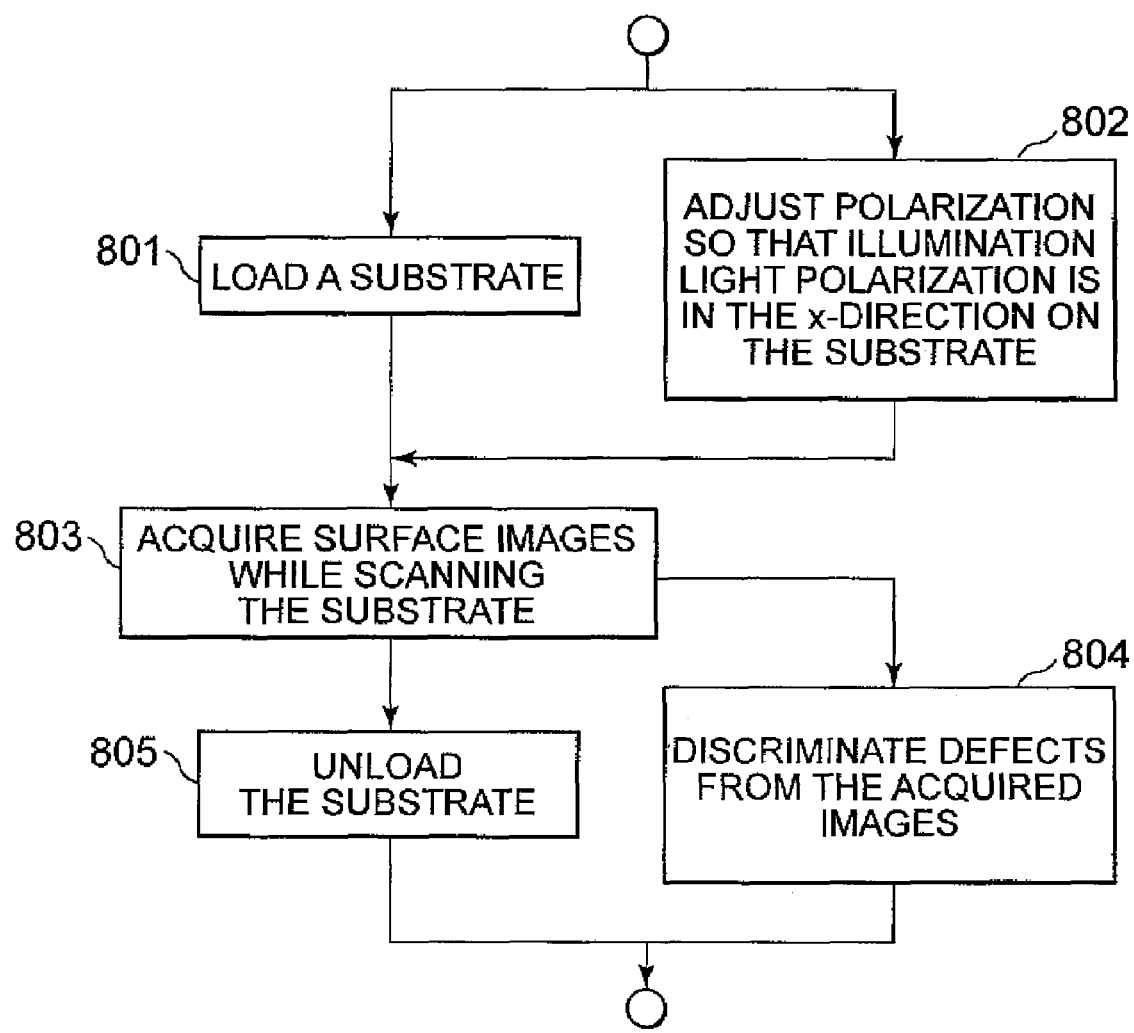
FIG. 8 is a diagram showing a first operation flow of the inspection apparatus according to the first embodiment of the present invention.
Figure 9:
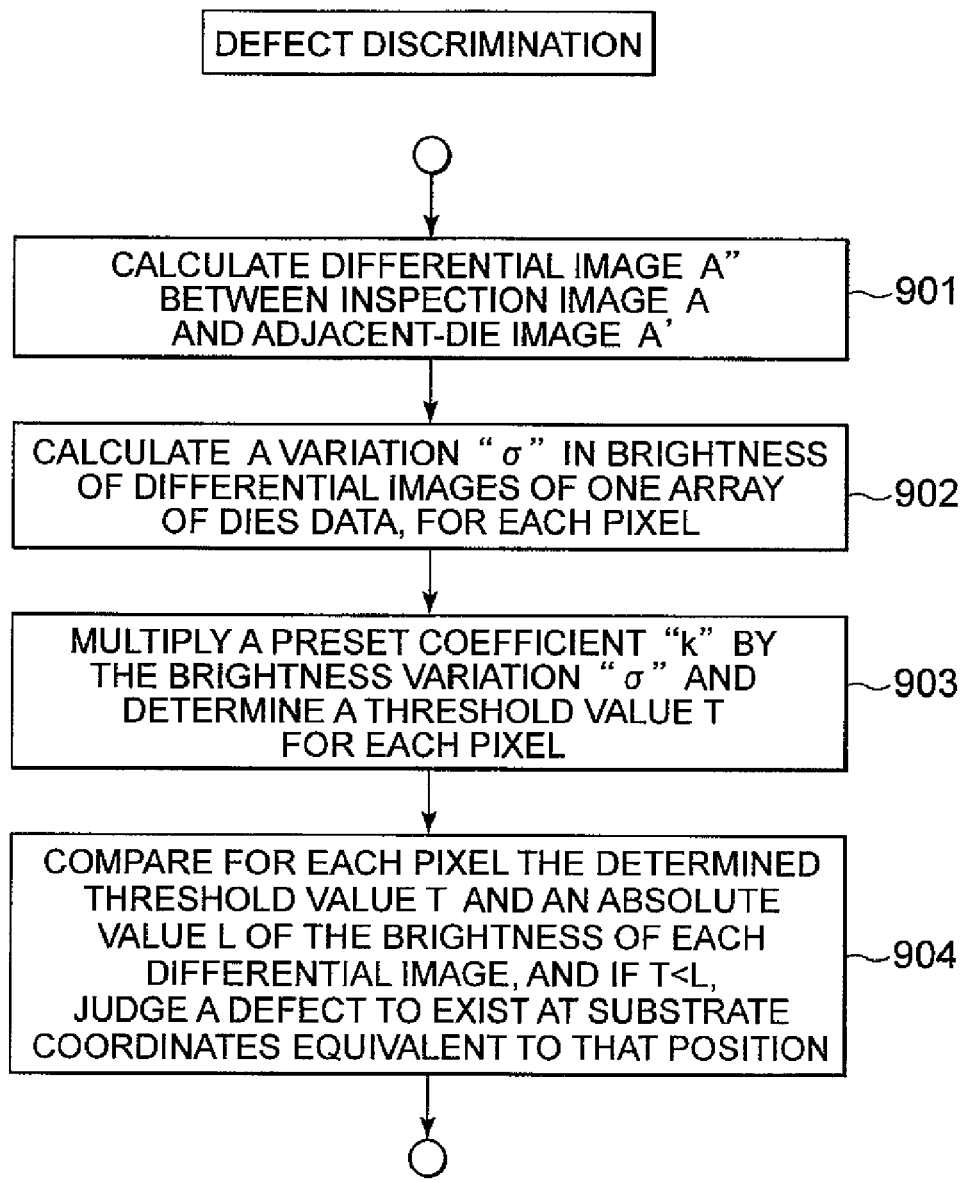
FIG. 9 is a diagram showing a defect discrimination process flow of the inspection apparatus according to the first embodiment of the present invention.

As shown in FIG. 8, the substrate 100 is loaded into the inspection apparatus 1 (step 801) and fixed to the substrate chuck 35 of the substrate conveying circuit 30. The inspection apparatus 1 performs control for minimum substrate inclination by operating in alignment mode. The inspection apparatus 1 also calculates origin coordinates of the substrate. Concurrently with or at substantially the same timing as the above control and calculation, the inspection apparatus 1 controls the polarization control unit 13 via the unit controller 82 (step 802) so that the polarized state of the illumination light essentially matches the x-direction, that is, a scanning direction of the x-direction stage 31, on the substrate.

After that, the fixed substrate 100 is scanned by means of the x-direction stage 31 and a surface image of the substrate 100 is acquired by the detection optics 20 synchronized with the scan (step 803). The acquired surface image is then compared with a surface image acquired at the same imaging position of adjacent dies in order to discriminate whether a defect is present there (step 804). Scanning in the x-direction with step movement in the y-direction is repeated and upon completion of total substrate surface image acquisition, the substrate 100 is unloaded from the inspection apparatus 1 (step 805).

Of the above inspection flow sequence, operation flow of the detection optics 20 and image-processing circuit 60 is described in detail below.

In the detection optics 20, the diffracted light and scattered light that occur on the surface of the substrate 100 undergo photoelectric conversion and A/D conversion by the photosensor 25 and the A/D conversion unit 26, respectively. Thus, a surface image is obtained and the surface image data is transmitted to the adjacent die-to-die image position error information calculation unit 61. The adjacent die-to-die image position error information calculation unit 61 then calculates adjacent die-to-die image position error information in ⅒ pixel units and transmits calculation results to the data processing unit 62. The data processing unit 62 calculates a die-to-die differential image based on the received surface image and position error information, and discriminates/detects defects using the differential image. Coordinates and feature quantities of detected defects, and images of each defect are collectively transmitted to the control and processing circuit as the defect information.

Additionally, defect discrimination process flow in the inspection flow sequence is described in detail below with reference to FIG. 9.

First, inspection image A, adjacent-die image A' that becomes a reference image, and information on a position error between both images are used to calculate differential image A", and this operation is repeated to obtain one x-stage moving scan of data (step 901). Hereinafter, one x-stage moving scan of data is called one array of dies data. Next, a variation "σ" in brightness between the differential images obtained at a location corresponding to the same section of one array of dies data is calculated on a pixel-by-pixel basis (step 902). After this, a coefficient "k" that has been preset using a user interface is multiplied by the above brightness variation "σ" to determine a defect detection threshold value T for the pixels of interest (step 903). The determined defect detection threshold value T and an absolute value of the brightness of each differential image are compared for each pixel, and if the absolute value L of the brightness of the differential image A" is greater than the defect detection threshold value T, a defect is judged to exist at the coordinate on the substrate 100 that is equivalent to the particular pixel position (step 904).

The above process flow is repeated for images in a previously designated inspection region or for all acquired inspection images on the substrate 100, whereby defects on the substrate 100 are discriminated and the defect coordinates are calculated.

In this defect discrimination process flow, after the differential image A" of the adjacent-die images has been obtained, the brightness variation "σ" is determined, then the threshold value T is calculated from the brightness variation "σ", and defects are discriminated using the threshold value T. However, defects may be discriminated by combining the brightness levels of two adjacent images and then calculating a differential image similarly to the above process, or by using data voted in a multidimensional space having in an axial direction the brightness, contrast, and other features of the inspection image and reference image. Any defect discrimination method using die-to-die brightness differential information can be used as appropriate. In addition, the differential image to be calculated does not always need to be that of any adjacent dies and can be that of any dies positioned remotely from each another.

Figure 13:
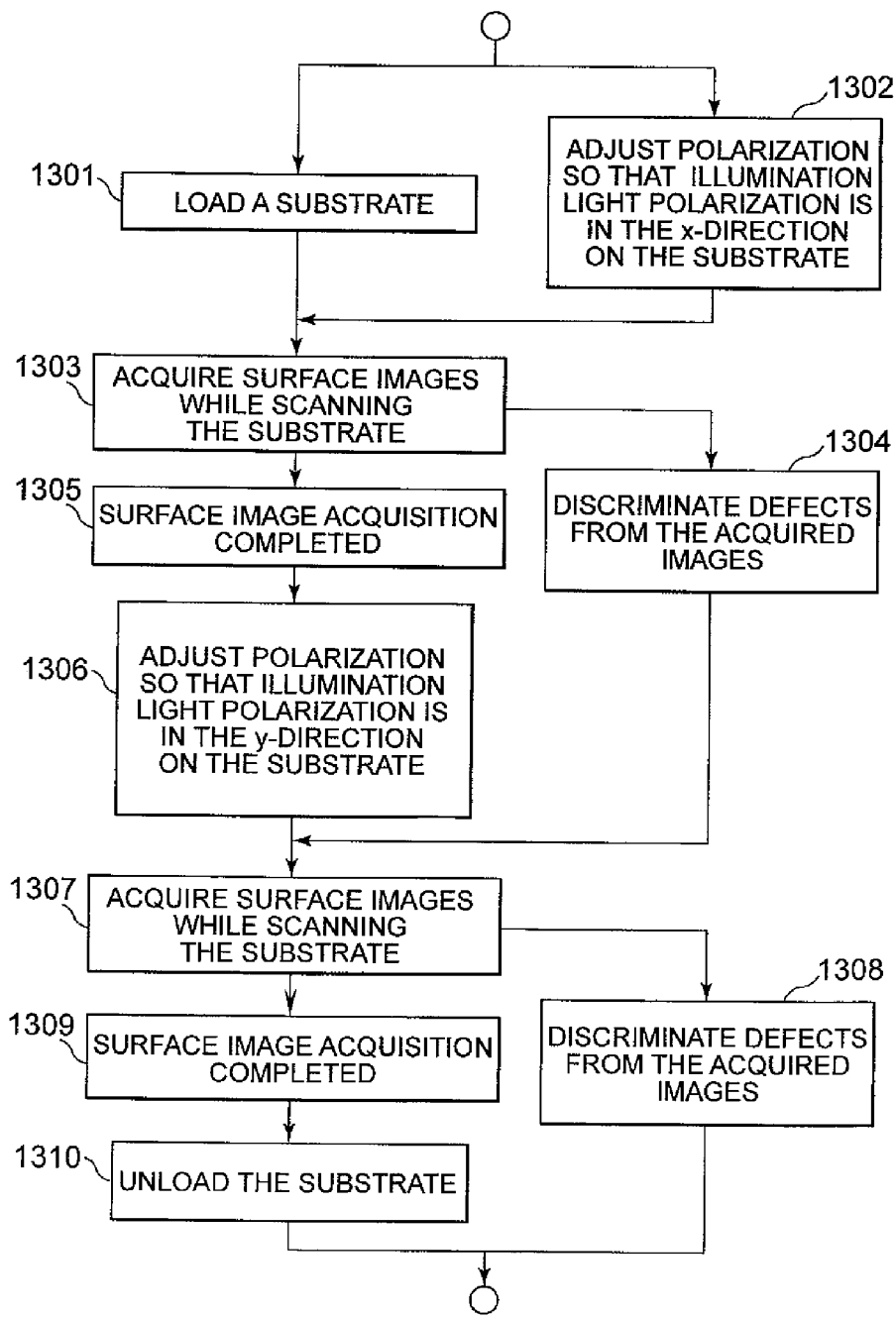
FIG. 13 is a diagram showing a second operation flow of the inspection apparatus according to the first embodiment of the present invention.

Other inspection process steps for the inspection apparatus according to the present embodiment are described below with reference to FIG. 13. The substrate 100 is loaded into the inspection apparatus 1 (step 1301) and fixed to the substrate chuck 35 of the substrate conveying circuit 30. Concurrently with or at substantially the same timing as the mounting of the substrate, the inspection apparatus 1 controls the polarization control unit 13 via the unit controller 82 (step 1302) so that the polarized state of the illumination light essentially matches the x-direction, that is, the scanning direction of the x-direction stage 31, on the substrate. After that, the fixed substrate 100 is scanned by means of the x-direction stage 31, and a surface image of the substrate 100 is acquired by the detection optics 20 synchronized with the scan (step 1303). The acquired surface image is then compared with a surface image acquired at the same imaging position of adjacent dies in order to discriminate whether a defect is present there (step 1304).

Next, the entire surface of the substrate 100 is scanned and upon completion of its surface image acquisition (step 1305), the unit controller 82 controls the polarization control unit 13 so that the polarized state of the illumination light substantially matches the y-direction, that is, the scanning direction of the y-direction stage 32 (step 1306), on the substrate. After that, the fixed substrate 100 is scanned by means of the x-direction stage 31, and a surface image of the substrate 100 is acquired by the detection optics 20 synchronized with the scan (step 1307). The acquired surface image is then compared with a surface image acquired at the same imaging position of adjacent dies in order to discriminate whether a defect is present there (step 1308).

The entire surface of the substrate 100 is scanned and upon completion of its surface image acquisition (step 1309), the substrate 100 is unloaded (step 1310).

The substrate region to be inspected is where patterns parallel to the x-direction and patterns parallel to the y-direction are mixedly present. In this inspection process flow, any short-circuiting defect at the bottom of the patterned section can be detected very accurately over the entire substrate surface by varying the polarized state and acquiring the light scattered from the substrate 100. While an example of scanning the entire substrate surface twice has been shown in the description of the above process flow, scanning the same place twice during the inspection can be avoided by changing the polarized state appropriately according to the particular arrangement of the patterns on the substrate 100.

In this way, any short-circuiting defect at the bottom of the patterned section can be detected with high sensitivity in the first embodiment of the inspection apparatus according to the present invention.

Next, modifications of the first embodiment of the inspection apparatus according to the present invention are described below.

Figure 10:
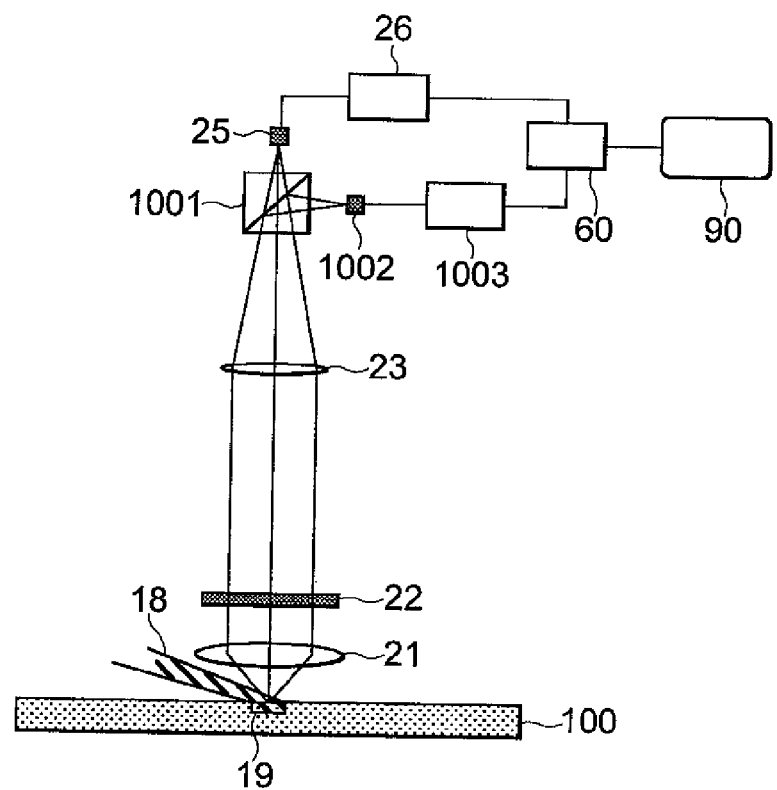
FIG. 10 is a diagram showing a first modification of the detection optics in the first embodiment of the inspection apparatus according to the present invention.

A first modification of the detection optics 20 in the first embodiment is first described with reference to FIG. 10. The light scattered from the region 19 on the substrate 100 that has been irradiated with the beam of illumination light, 18, is passed through the objective lens 21, the spatial filter 22, the image-forming lens 23, and a polarizing beam splitter 1001, thus forming a substrate surface image on the first photosensor 25 and a second photosensor 1002. At this time, since the polarizing beam splitter 1001 is inserted, the light of different polarized components forms the image in separate form on the first photosensor 25 and on the second photosensor 1002. After analog-to-digital conversion of output signals of the first photosensor 25 and the second photosensor 1002 by A/D conversion units 26 and 1003, respectively, defects are detected by the image-processing circuit 60 and then defect detection results are displayed on a screen or stored via the interface circuit 90.

Figure 11:
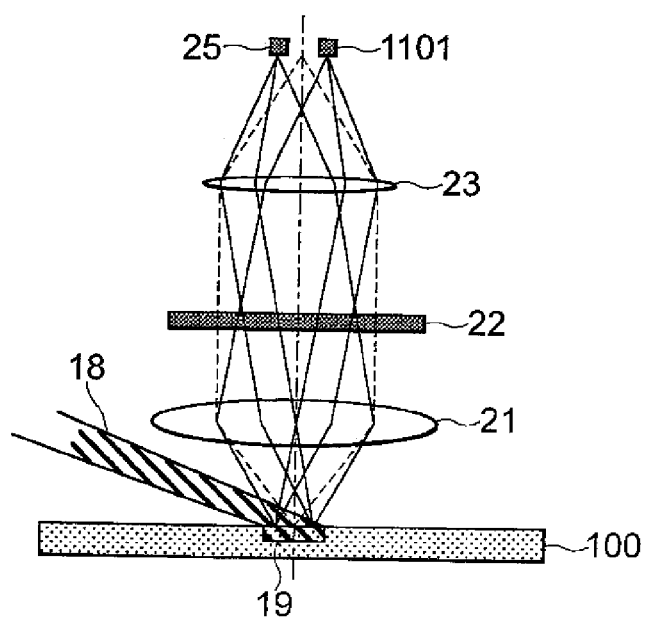
FIG. 11 is a diagram showing a second modification of the detection optics in the first embodiment of the inspection apparatus according to the present invention.

A second modification of the detection optics 20 is next described with reference to FIG. 11. The light scattered from the region 19 on the substrate 100 that has been irradiated with the beam of illumination light, 18, is passed through the objective lens 21, the spatial filter 22, and the image-forming lens 23, thus forming a surface image on the first photosensor 25 and a second photosensor 1101 spaced from the first photosensor 25. During the formation of the image, the scattered light from the substrate surface, detected by the first photosensor 25 and the second photosensor 1101, differs in position of the substrate surface from which the light was scattered.

Operation flow of the substrate surface image-forming section is next described below with reference to FIGS. 14A and 14B, wherein the distance between the first photosensor 25 and the second photosensor 1101 is expressed as "d" and an optical magnification of the detection optics 20 is expressed as A.

FIG. 14A shows first operation flow. First, the substrate surface is simultaneously imaged at certain timing using the first photosensor 25 and the second photosensor 1101 (step 1401). Next after the stage circuit has moved the substrate through a distance of 2×d/A, the surface of the sample is once again imaged at the same time using the first photosensor 25 and the second photosensor 1101 (step 1402). At this time, sequential positioning and defect detection are performed in the image-processing circuit (step 1403). The entire substrate surface is imaged by repeating this sequence for all sections down to the substrate edges (step 1404). Image processing in this first operation flow by the use of the second modification of the detection optics 20 allows rapid acquisition of a surface image at a double speed, compared with a method using one photosensor.

FIG. 14B shows second operation flow. First, the surface of a sample is simultaneously imaged at certain timing using the first photosensor 25 and the second photosensor 1101 (step 1405). Next after the stage circuit has moved the sample through a distance of d/A, the surface of the sample is once again imaged at the same time using the first photosensor 25 and the second photosensor 1101 (step 1406). In this operational sequence, one specific position on the surface is imaged twice in all, once on the first photosensor 25 and the second photosensor 1101 each. The image-processing circuit performs processing of the two images, such as addition or averaging, to acquire a substrate surface image minimized in electrical noise, and detect defects (step 1407). The entire substrate surface is imaged by repeating this sequence for all sections down to the substrate edges (step 1408). Image processing in this second operation flow by the use of the second modification of the detection optics 20 allows acquisition of a substrate surface image minimized in electrical noise, and hence, high-sensitivity detection of defects.

Figure 12:
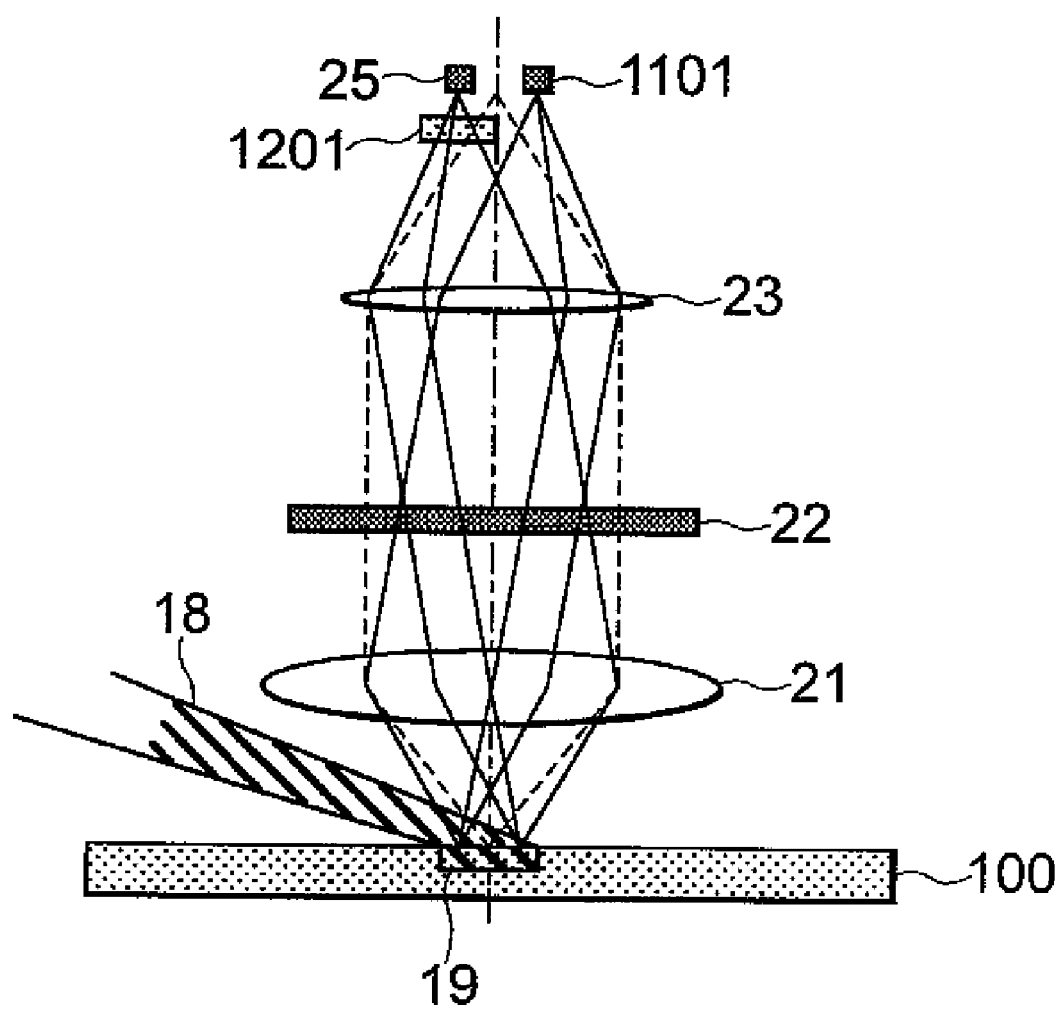
FIG. 12 is a diagram showing a third modification of the detection optics in the first embodiment of the inspection apparatus according to the present invention.

A third modification of the detection optics 20 is next described with reference to FIG. 12. The third modification includes an attenuator 1201 inserted in front of one photosensor 25 in the second modification. When the operation flow in FIG. 14B is applied to the third modification, one specific position on the surface is likewise imaged twice in all, once on the first photosensor 25 and the second photosensor 1101 each, but since the amount of light detected differs between the photosensors, a dynamic range, usually around 100, of the photosensors can be extended by processing the two images as appropriate. The dynamic range can likewise be extended by assigning different sensitivities to the first photosensor 25 and second photosensor 1101 in the second modification.

Second Embodiment

Figure 15:
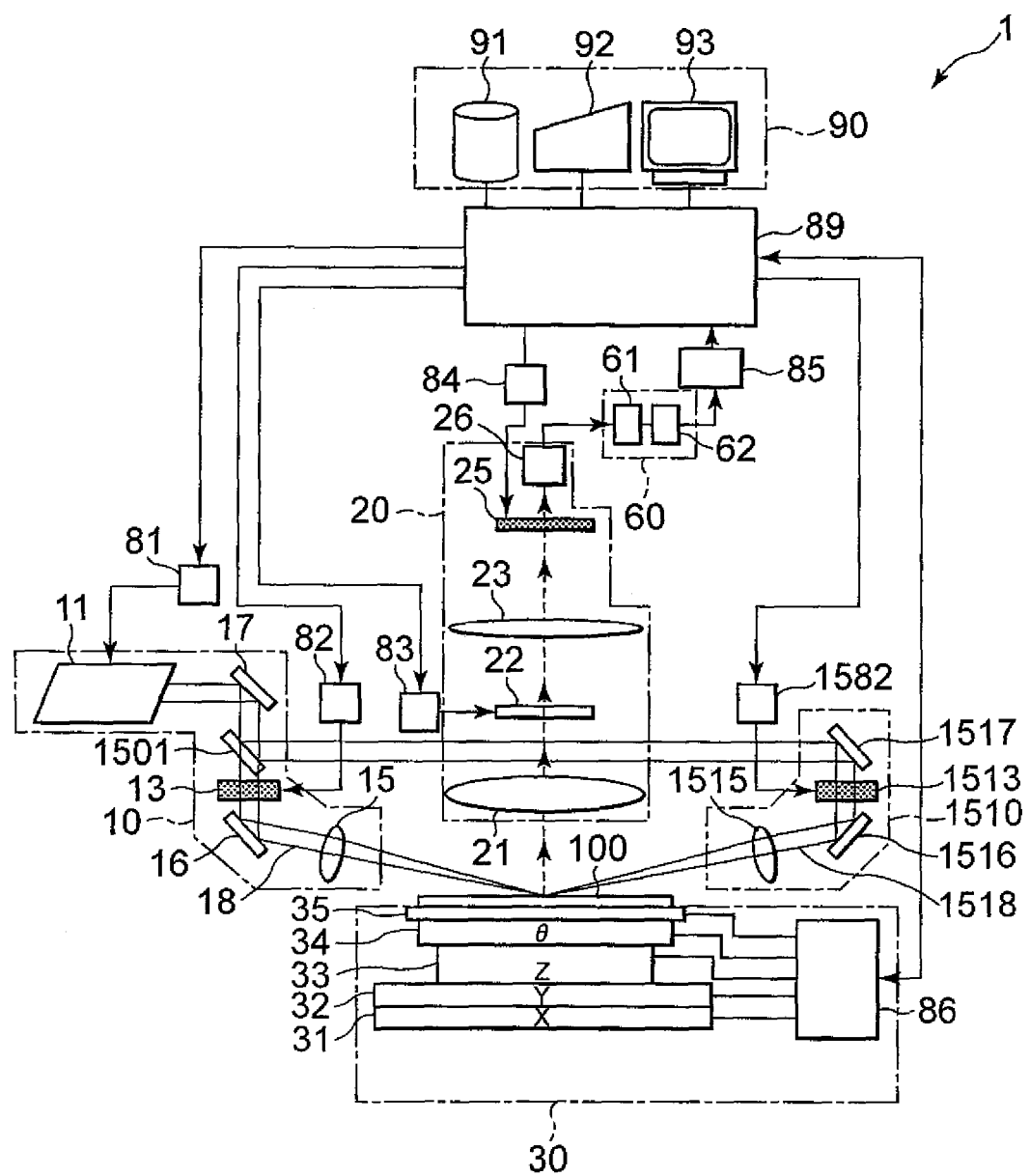
FIG. 15 is a diagram showing a second embodiment of an inspection apparatus according to the present invention.

A second embodiment of an inspection apparatus according to the present invention is described below with reference to FIG. 15, a block diagram of the inspection apparatus. In the description below, the same constituent elements as those of the first embodiment are omitted and focus is placed primarily upon differences. The inspection apparatus 1 includes, as appropriate, first illumination optics 10, second illumination optics 1510, detection optics 20, a substrate conveying circuit 30, a focal measuring circuit 50 (not shown), an image-processing circuit 60, a control and processing circuit, and an interface circuit 90.

The first illumination optics 10 is constructed using, as appropriate, a laser light source 11, reflecting mirrors 16 and 17 that guide in a required direction the light emitted from the laser light source 11, a polarization control unit 13, a condensing lens 15, and an optical splitting element 1501 provided between the reflecting mirror 17 and the polarization control unit 13.

Also, the second illumination optics 1510 is constructed using, as appropriate, reflecting mirrors 1516 and 1517 by which the light from the laser light source 11 has been split by the optical splitting element 1501 is guided in the required direction, a polarization control unit 1513 controlled by a unit controller 1582, and a condensing lens 1515. Although an example of splitting laser light using one laser light source 11 is shown in the present embodiment, the first illumination optics and the second illumination optics can each use a different laser light source as appropriate.

Light that has exited the light source 11 is reflected by the reflecting mirror 17 and then split into two beams of light by the optical splitting element 1501. One of the beams enters the first illumination optics 10, and the other beam enters the second illumination optics 1510.

First, the beam of light that passes through the first illumination optics is described below. A polarizing direction of the beam is controlled by the polarization control unit 13 to ensure rectilinear polarization and obtain the light polarized in either an x-direction or a y-direction on a substrate 100, then the beam is changed into a sheet-shaped beam 18 by the condensing lens 15 such as a cylindrical lens, and the surface (illumination region 19, not shown) of the substrate 100 is irradiated.

Next, the beam of light that passes through the second illumination optics 1510 is described below. As with the first illumination optics, the second illumination optics 1510 controls the polarizing direction of the beam by means of the polarization control unit 1513 to ensure rectilinear polarization and obtain the light polarized in either the x-direction or the y-direction on the substrate 100, then changes the beam into the sheet-shaped beam 1518 via the condensing lens 1515 such as a cylindrical lens, and irradiates the surface (illumination region 1519, not shown) of the substrate 100.

In the present embodiment, if the scan of the substrate is in the x-axis direction, the region illuminated in sheet-shaped form on the substrate will be long in a direction orthogonal to the scanning direction of the substrate, that is, substantially in the y-axis direction. The polarization control units 13 and 1513 are controlled so that the regions 19 and 1519 illuminated will essentially match and so that the polarizing directions 19α·β and 1519α·β on the substrate surface will also essentially match.

Of all light scattered from the irradiation regions 19 and 1519 of the illumination light on the substrate, only light that has entered the objective lens 21 is converted into image form on the photosensor 25 through the spatial filter 22 and the image-forming lens 23. The photosensor 25 is driven by a sensor driver 84 to operate synchronously with digital conversion by the A/D conversion unit 26, synchronized with the output of the photosensor 25. Digital conversion results are transmitted to the adjacent die-to-die image position error information calculation unit 61. Position matching is performed by the image position error information calculation unit 61, and defect discrimination/detection using a position-matched die-to-die differential image is performed by the data processing unit 62. Detected defect information is merged and classified by the defect information-processing unit 85. Merging and classification results are aggregated by the control unit 89 and then the aggregated data is transferred to the interface circuit 90 for saving, screen display, or the like.

Figure 16A:
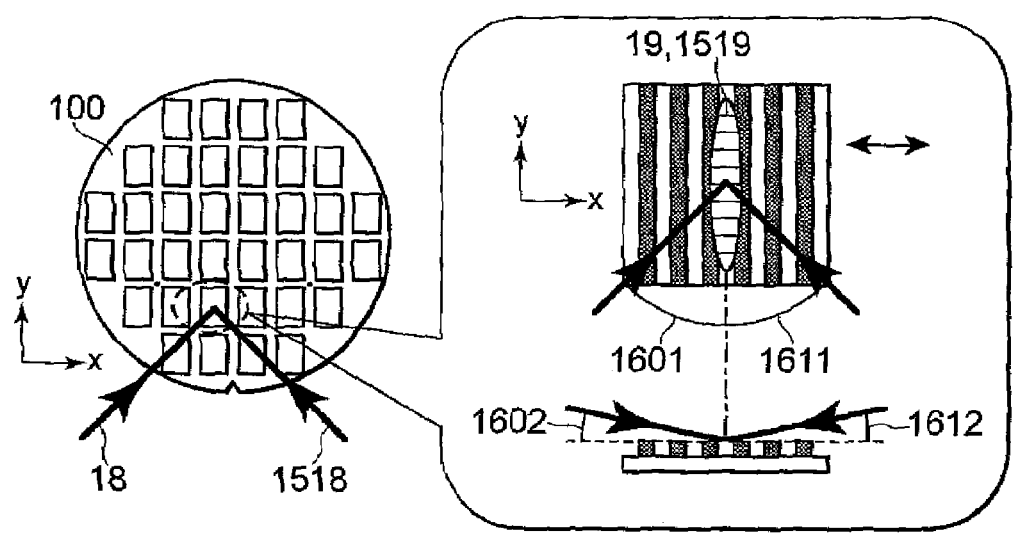
FIG. 16A is a diagram that shows details of a substrate illumination region in an identical-region dual-spot illumination scheme of a second embodiment of an inspection apparatus according to the present invention.
Figure 16B:
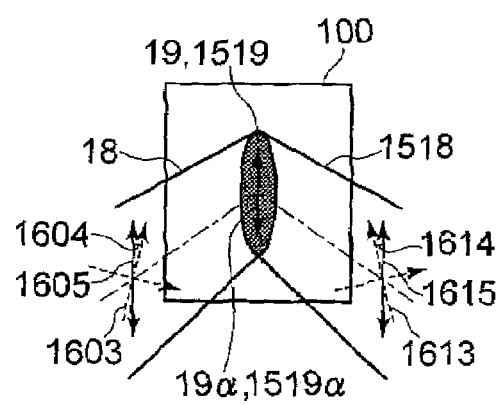
FIG. 16B is a diagram that shows a first example of a substrate illumination region in the identical-region dual-spot illumination scheme of the second embodiment of the inspection apparatus according to the present invention.
Figure 16C:
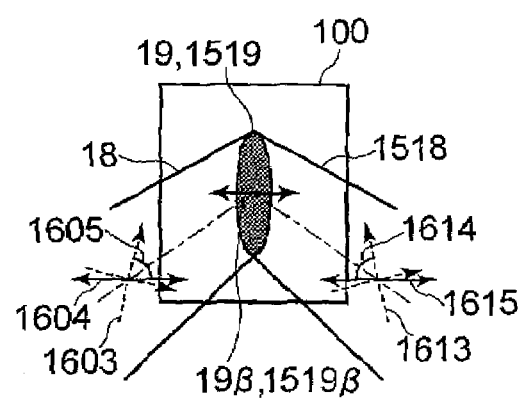
FIG. 16C is a diagram that shows a second example of a substrate illumination region in the identical-region dual-spot illumination scheme of the second embodiment of the inspection apparatus according to the present invention.

Here, conditions (parameters) relating to the illumination light emitted to a neighboring region of the substrate 100 according to the present embodiment including the two sets of illumination optics, 10 and 1510, are described with reference to FIGS. 16A to 16C. As shown in FIG. 16A, the sheet-shaped beam 18 from the first illumination optics 10 irradiates the illumination region 19 on the surface of the substrate 100 under conditions of an illumination azimuth angle 1601 and an illumination elevation angle 1602. Similarly, the sheet-shaped beam 1518 from the second illumination optics 1510 irradiates the illumination region 1519 of the substrate surface that overlaps the illumination region 19, under conditions of an illumination azimuth angle 1611 and an illumination elevation angle 1612. In the present embodiment, if the scan of the substrate is in the x-axis direction, the region illuminated in sheet-shaped form on the substrate will be long in the direction orthogonal to the scanning direction of the substrate, that is, substantially in the y-axis direction. Also, the polarization control units 13 and 1513 and the reflecting mirrors 16 and 1516 are controlled so that the regions 19 and 1519 illuminated will essentially match and so that as shown in FIG. 16B, the polarizing direction 19α of the sheet-shaped beam 18 on the substrate surface and the polarizing direction 1519α of the sheet-shaped beam 1518 will essentially match, or as shown in FIG. 16C, the polarizing direction 19β of the sheet-shaped beam 18 and the polarizing direction 1519β of the sheet-shaped beam 1518 will essentially match. The polarization control units 13 and 1513 are controlled to ensure that one of two rotational angles from an illumination axis 1603 for S-polarized illumination will be a rotational angle 1604 calculated from the illumination azimuth angle 1601 and the illumination elevation angle 1602, and the other will be a rotational angle 1614 calculated from the illumination azimuth angle 1611 and the illumination elevation angle 1612. The polarizing directions 19α·β and 1519α·β of the two beams of light on the illumination regions 19 and 1519, respectively, can be essentially matched by the above control.

During conventional imaging, defects present on a side of a pattern or at the bottom thereof have only appeared as shadows. According to the present embodiment, however, illuminating one spot from two directions allows the detection of even these defects, and hence, highly accurate inspection of defects.

Operation flow of the present embodiment can apply, as appropriate, any one of the examples shown and described in the first embodiment.

Figure 17A:
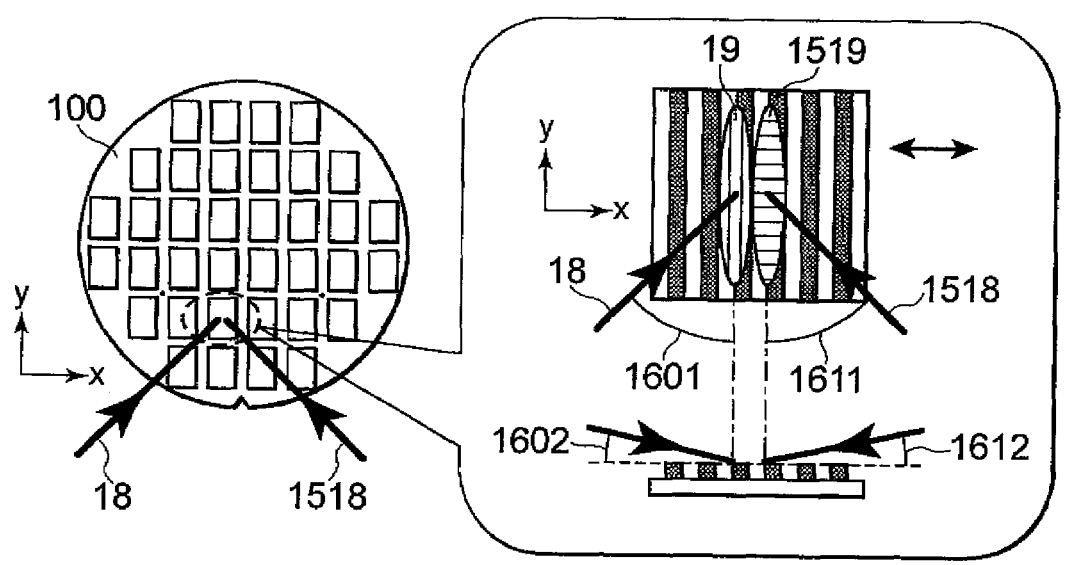
FIG. 17A is a diagram that shows details of a substrate illumination region in an adjacent-region dual-spot illumination scheme of the second embodiment of the inspection apparatus according to the present invention.
Figure 17B:
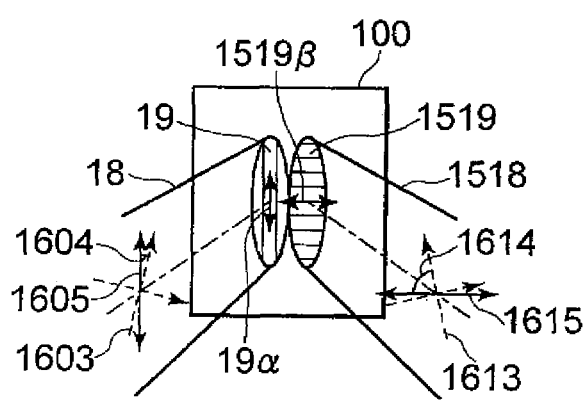
FIG. 17B is a diagram that shows a first example of a substrate illumination region in the adjacent-region dual-spot illumination scheme of the second embodiment of the inspection apparatus according to the present invention.

Next, an example of illuminating two different spots from two directions using the inspection apparatus of the present embodiment is described below with reference to FIGS. 17A and 17B. As shown in FIG. 17A, the sheet-shaped beam 18 from the first illumination optics 10 irradiates the illumination region 19 on the surface of the substrate 100 under the conditions of the illumination azimuth angle 1601 and the illumination elevation angle 1602. Similarly, the sheet-shaped beam 1518 from the second illumination optics irradiates the illumination region 1519 of the substrate surface that differs from the illumination region 19, under the conditions of the illumination azimuth angle 1611 and the illumination elevation angle 1612. If the scan of the substrate is in the x-axis direction, the region illuminated in sheet-shaped form on the substrate will be long in the direction orthogonal to the scanning direction of the substrate, that is, substantially in the y-axis direction. In addition, the polarization control units 13 and 1513 and the reflecting mirrors 16 and 1516 are controlled so that as shown in FIG. 17B, the polarizing directions 19α and 1519β on the substrate surface will be essentially orthogonal to each other. The polarization control units 13 and 1513 are controlled to ensure that one of two rotational angles from the illumination axis 1603 for S-polarized illumination will be the rotational angle 1604 calculated from the illumination azimuth angle 1601 and the illumination elevation angle 1602, and the other will be the rotational angle 1614 calculated from the illumination azimuth angle 1611 and the illumination elevation angle 1612. The polarizing directions 19α and 1519β of the two beams of light on the illumination regions 19 and 1519, respectively, can be made essentially orthogonal to each other by the above control.

According to the present embodiment, since two spots different from each other in polarized state are used to scan the substrate, defects present at the bottom of each pattern in the x-direction and at the bottom of each pattern in the y-direction can be detected during one scan. Although a combination between the polarizing direction 19α of the sheet-shaped beam 18 and the polarizing direction 1519β of the sheet-shaped beam 1518 has been presented in the present embodiment, the polarizing direction 19β of the sheet-shaped beam 18 and the polarizing direction 1519α of the sheet-shaped beam 1518 can be combined instead. In addition, the operation flow of the present embodiment can apply, as appropriate, any one of the examples presented in the first embodiment.

Next, modifications of the second embodiment of the inspection apparatus according to the present invention are described below.

A first modification of the detection optics 20 in the second embodiment is first described with reference to FIG. 18. The sheet-shaped beam 18 from the first illumination optics 10 irradiates the illumination region 19 on the surface of the substrate 100, and the sheet-shaped beam 1518 from the second illumination optics 1510 irradiates the illumination region 1519 on the surface of the substrate 100. The detection optics 20 is constructed to ensure that the regions 19 and 1519 on the substrate surface are made conjugate to the surfaces of the photosensor 25 and a photosensor 1801, respectively, via the objective lens 21, the spatial filter 22, and the image-forming lens 23. According to the first modification of the detection optics 20 in the second embodiment, the two regions 19 and 1519 that differ in illumination conditions such as the polarizing direction can be imaged using the photosensors 25 and 1801, respectively, and appropriate processing of these images allows optimal detection of defects. The two regions 19 and 1519 do not always need to be adjacent to each other and can be spaced through a predetermined distance 1802 from each other.

Figure 19:
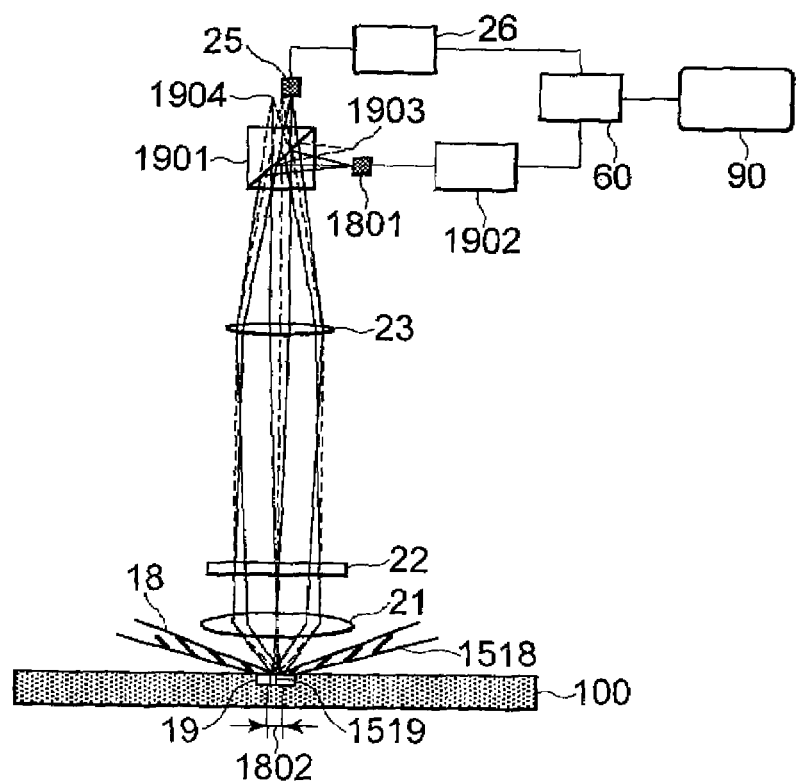
FIG. 19 is a diagram showing a second modification of the detection optics in the second embodiment of the inspection apparatus according to the present invention.

A second modification of the detection optics 20 in the second embodiment is next described with reference to FIG. 19. The light scattered from the region 19 on the surface of the substrate 100 that has been irradiated with the beam of illumination light, 18, likewise forms a substrate surface image on the photosensor 1801 and on a position 1904, via the image-forming optics 20, that is, the objective lens 21, the spatial filter 22, the image-forming lens 23, and a polarizing beam splitter 1901. At this time, since the polarizing beam splitter 1901 is inserted, the light of different polarized components forms the image in separate form on the photosensor 1801 and on the position 1904. Only the polarized components of the light that have been separated by the polarizing beam splitter 1901 are detected by the photosensor 1801. After analog-to-digital conversion of the polarized beams by an analog/digital conversion unit 1902, defects are detected by the image-processing circuit 60 and defect detection results are displayed on a screen or stored via the interface circuit 90. In the meantime, the light scattered from the region 1519 on the surface of the substrate 100 that has been irradiated with the beam of illumination light, 1518, likewise forms a substrate surface image on the photosensor 25 and on a position 1903, via the image-forming optics 20. At this time, since the polarizing beam splitter 1901 is inserted, the light of different polarized components forms the image in separate form on photosensor 45 and on position 47. Only the polarized components of the light that have been separated by the polarizing beam splitter 1901 are detected by the photosensor 25. After analog-to-digital conversion of the polarized beams by the analog/digital conversion unit 26, defects are detected by the image-processing circuit 60 and then defect detection results are transferred to the interface circuit 90 for screen display or storage. According to the present embodiment, even if the distance 1905 between the two regions, 19 and 1519, is not too long and both regions essentially overlap, only the desired light of polarized components can be detected since the polarizing beam splitter 1901 is used.

Figure 20:
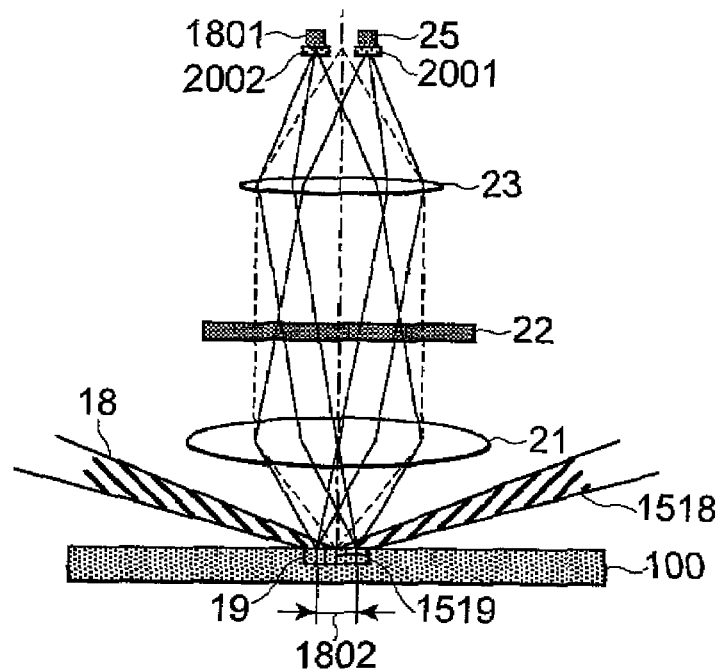
FIG. 20 is a diagram showing a third modification of the detection optics in the second embodiment of the inspection apparatus according to the present invention.

A third modification of the detection optics 20 in the second embodiment is next described with reference to FIG. 20. The light scattered from the region 19 on the surface of the substrate 100 that has been irradiated with the beam of illumination light, 18, forms a substrate surface image on the photosensor 25 via the image-forming optics 20, that is, the objective lens 21, the spatial filter 22, and the image-forming lens 23. A polarizing film 2001 is affixed to the surface of the photosensor 25. Thus, the photosensor 25 can detect the substrate surface image created from the scattered light of polarized components capable of penetrating the polarizing film 2001. The above also applies to the light scattered from the region 1519 on the substrate surface that has been irradiated with the illumination beam of light, 18. That is to say, results of image forming on the surface of the photosensor 1801 can likewise be detected through the detection optics 20. In the third modification, affixing a polarizing film 2002 to the surface of the photosensor 1801 also allows the photosensor 25 to detect the substrate surface image created from the scattered light of polarized components capable of penetrating the polarizing film 2002.

Figure 21:
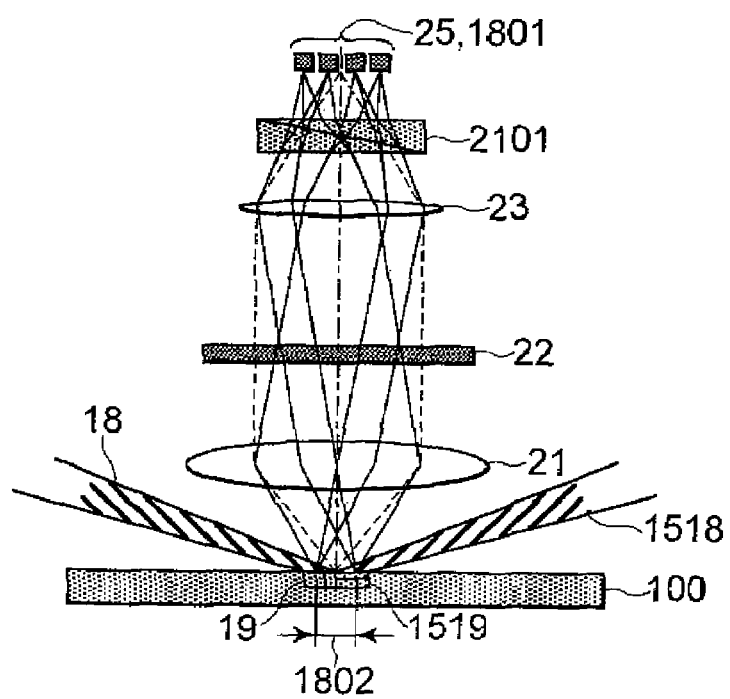
FIG. 21 is a diagram showing a fourth modification of the detection optics in the second embodiment of the inspection apparatus according to the present invention.

A fourth modification of the detection optics 20 in the second embodiment is next described with reference to FIG. 21. The light scattered from the region 19 on the surface of the substrate 100 that has been irradiated with the beam of illumination light, 18, forms a substrate surface image on the photosensor via the image-forming optics 20, that is, the objective lens 21, the spatial filter 22, the image-forming lens 23, and a Wollaston prism 2101. Similarly, the scattered light originating from illumination beam of light, 1518, also forms an image on the photosensor. In the present embodiment, scattered light of different polarized components is separated into two beams by using the Wollaston prism 2101. The two beams of light form images at positions slightly shifted from each other on the photosensor surface. In the present embodiment, the photosensor is constituted by two line sensors so that both polarized components of each scattered light are detected by the line sensors respectively.

Figure 22:
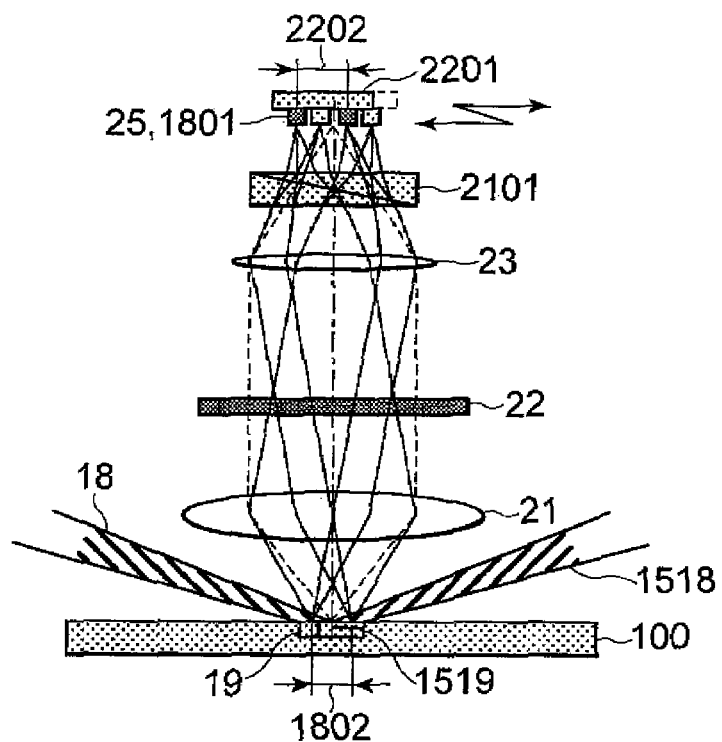
FIG. 22 is a diagram showing a fifth modification of the detection optics in the second embodiment of the inspection apparatus according to the present invention.

A fifth modification of the detection optics 20 in the second embodiment is next described with reference to FIG. 22. The present modification, although substantially the same as the above-described fourth modification in configuration, differs in that the photosensors 25 and 1801 are each constituted by one line sensor and in that both line sensors are fixed to the surface of a base 2201. The base 2201 can be translated in the array direction of the illumination beam irradiation regions through the same distance 2202 as the distance between two images shifted in a transverse direction by the Wollaston prism 2101. Such translation of the base 2201 allows independent detection of each beam of different polarized components that has been separated and imaged by the Wollaston prism 2101. The amount of transverse shift by the Wollaston prism 2101 is also the same as for the illumination beam of light, 1518, scattered from the irradiation region 1519 on the substrate surface. Even with the photosensors 25 and 1801 fixed to the base 2201, therefore, each beam of different polarized components that was separated and imaged by the Wollaston prism 2101 can be detected separately.

Figure 23:
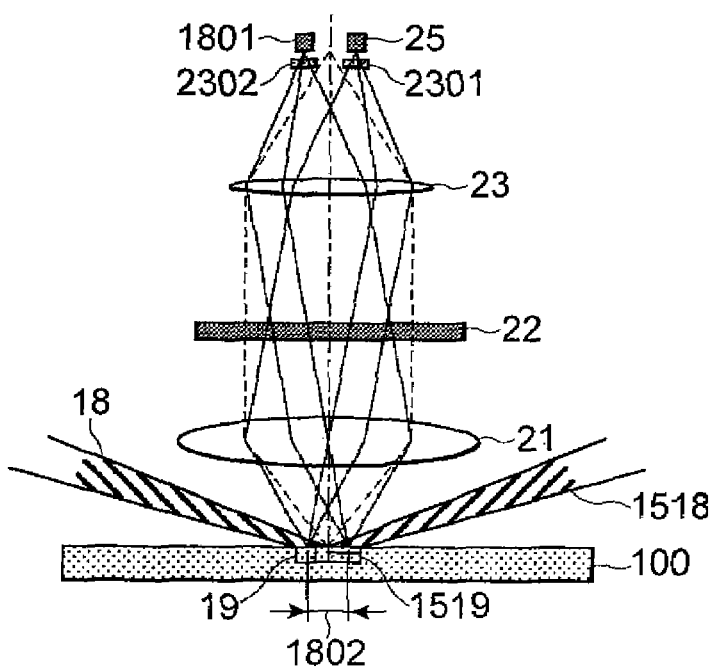
FIG. 23 is a diagram showing a sixth modification of the detection optics in the second embodiment of the inspection apparatus according to the present invention.

A sixth modification of the detection optics 20 in the second embodiment is next described with reference to FIG. 23.

Figure 18:
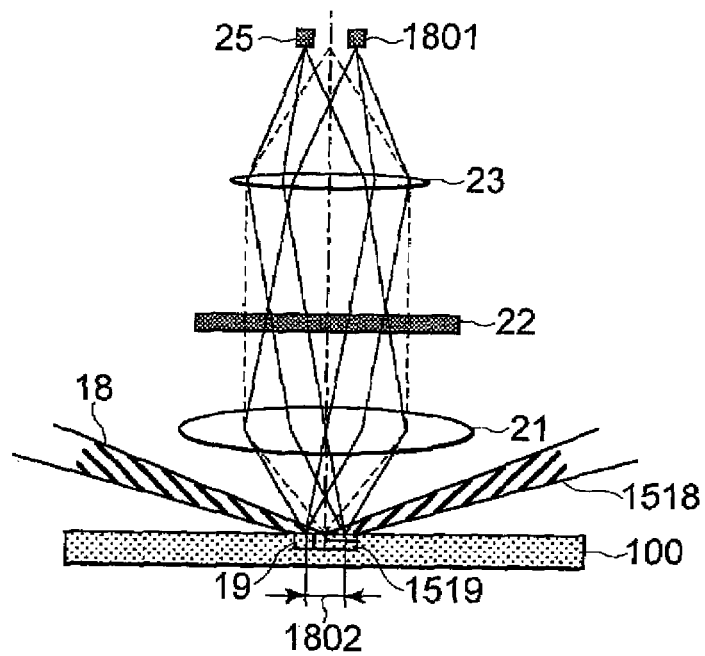
FIG. 18 is a diagram showing a first modification of the detection optics in the second embodiment of the inspection apparatus according to the present invention.

The present modification, although substantially the same as the first modification of the detection optics 20 in the second embodiment of FIG. 18 in terms of configuration, differs in that beam analyzers 2301 and 2302 are respectively arranged between the image-forming lens 23 and the photosensor 25 and between the image-forming lens 23 and the photosensor 1801. According to the present embodiment, rotating the arranged analyzers 2301 and 2302 in any polarizing direction allows the photosensors 25 and 1801 to detect surface images of the substrate 100 that are created by scattered light of desired polarized components.

Figure 24:
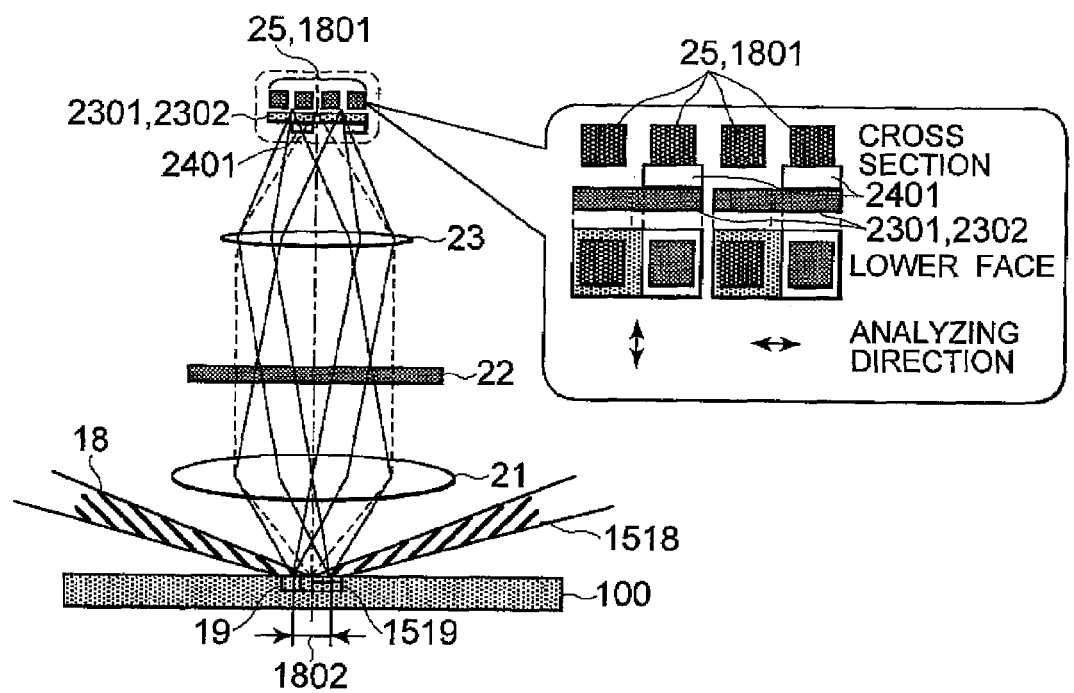
FIG. 24 is a diagram showing a seventh modification of the detection optics in the second embodiment of the inspection apparatus according to the present invention.

A seventh modification of the detection optics 20 in the second embodiment is next described with reference to FIG. 24. As with the sixth modification described above, the present modification includes the beam analyzers 2301 and 2302, and rotating these analyzers in any polarizing direction allows the photosensors to detect surface images of the substrate 100 that are created by the scattered light of the desired polarized components. Additionally in the present embodiment, the photosensors 25 and 1801 are both constituted by two line sensors proximate to each other. The two line sensors are both arranged so that the regions 19 and 1519 lie within image-forming regions of the detection optics 20. One of the two line sensors further includes an optical attenuation film 2401 affixed to the surface, thus ensuring a wide dynamic range in the entire corresponding photosensor.

Figure 25:
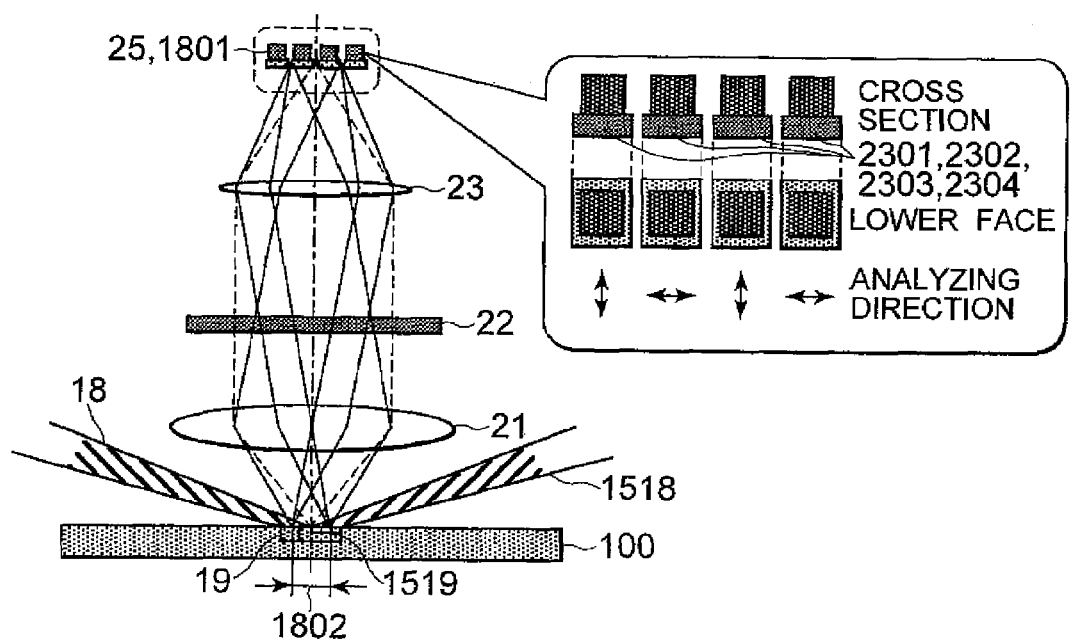
FIG. 25 is a diagram showing an eighth modification of the detection optics in the second embodiment of the inspection apparatus according to the present invention.
Figure 26:
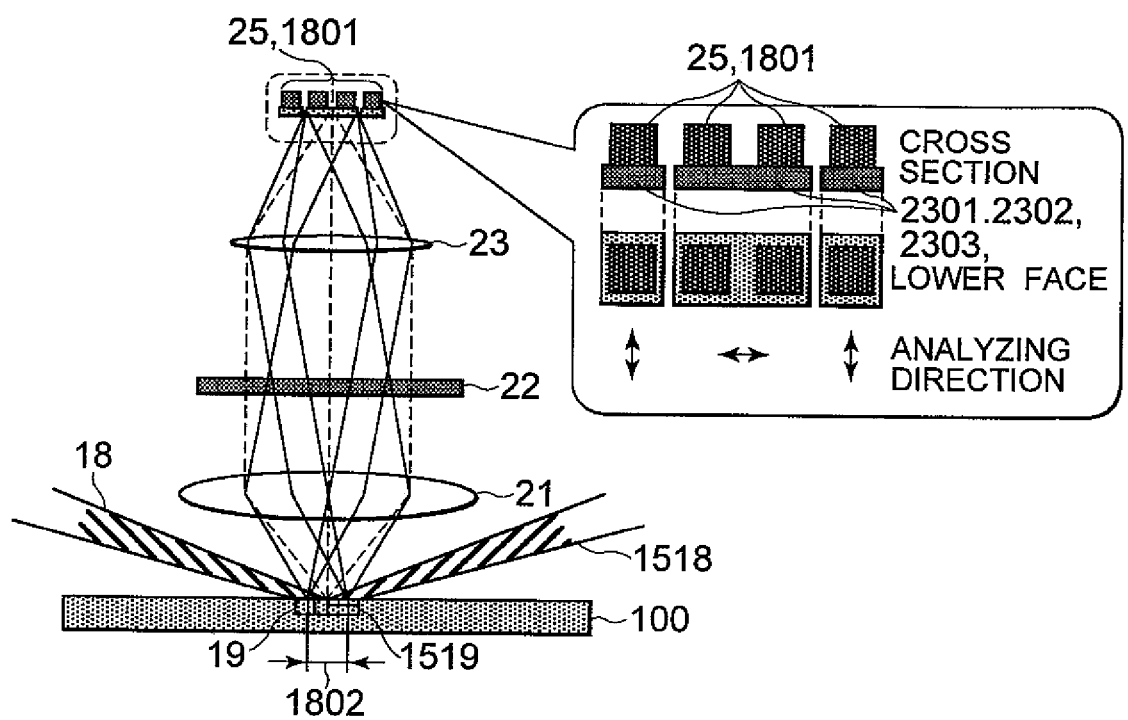
FIG. 26 is a diagram showing a ninth modification of the detection optics in the second embodiment of the inspection apparatus according to the present invention.

An eighth modification of the detection optics 20 in the second embodiment is next described with reference to FIG. 25. The beams of light scattered from the regions 19 and 1519 on the surface of the substrate 100 form a substrate surface image on the photosensors 25 and 1801, respectively, via the objective lens 21, the spatial filter 22, the image-forming lens 23, and beam analyzers 2301, 2302, 2303, and 2304. The photosensors 25 and 1801 in the present embodiment are both constituted by two line sensors proximate to each other. One of the two line sensors is disposed so that the region 19 lies within one image-forming region of the detection optics 20, and the other line sensor is disposed so that the region 1519 lies within another image-forming region of the detection optics 20. In addition, each line sensor includes a polarizing film affixed thereto, thus allowing the entire photosensors 25 and 1801 to detect the scattered light having different polarized components. In the present embodiment, the polarizing film is affixed to the surface of the photosensor. Instead of the polarizing film, however, a beam analyzer may be disposed between the photosensor and the image-forming lens. Furthermore, in a ninth modification of the detection optics 20 in the second embodiment, the detection optics 20 may be constructed so that as shown in FIG. 26, the number of polarizing films to be affixed can be reduced by matching the polarized components that the two sensors in the middle detect.

The detection optics 20 in each modification described above can be of any appropriate type selected according to desired conditions, and each operation flow based on the detection optics is substantially the same as the operation flow described in the first embodiment.

As described above, the inspection apparatus and inspection method according to the present invention are intended to detect and discriminate defects by comparing images of any two adjacent dies present at the same coordinate positions thereof in the die regions, and calculating a differential image from the images; wherein acquiring the images of at least two dies existing at the same positions by performing one scan with the x-direction stage allows reduction of the difference between both images due to the scan, and thus high-sensitivity detection of even a short-circuiting defect present at the bottom of a vertically longer pattern.

While the present invention has been described in detail above in accordance with embodiments, the embodiments do not limit the invention and various changes, modifications, or combinations can be performed without departing from the scope of the invention.

A defect inspection method and defect inspection apparatus capable of achieving highly accurate detection of even a short-circuiting defect present at the bottom of a vertically longer pattern are provided according to the present invention.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes that come within the meaning and range of equivalency of the claims are therefore intended to be embraced therein.

What is claimed is:

1. An apparatus for inspecting a substrate surface, the apparatus comprising:
   illumination optics for irradiating the substrate surface linearly with rectilinearly polarized light from an oblique direction;
   detection optics for acquiring images based on beams of light scattered from the substrate surface irradiated with the polarized light; and
   means for comparing an image selected as an inspection image from the plurality of substrate surface images that the detection optics has acquired, and another image selected from the plurality of substrate surface images as a reference image different from the inspection image to detect a defect;
   wherein the illumination optics includes polarization control means for controlling a polarizing direction of the light according to a direction orthogonal to a lengthwise direction of patterns of the substrate, and the polarization control means inclines the polarized light a angle to an orthogonal direction to a incidence plane of the polarized light, in which $$\alpha = \tan^{-1}\left(\frac{\tan\phi}{\cos\theta}\right)$$

where α is azimuth angle at which rectilinearly polarized light enters, ϕ is rotation angle in x-y plane and θ is elevation angle; and
   wherein the illumination optics is constructed to irradiate the substrate at an azimuth angle inclined through 15° to 75° to the scanning direction of the substrate.

2. The inspection apparatus according to claim 1,
   wherein the defect detection means detects the defect by using the inspection image and the reference image and calculating a position error between the inspection image and the reference image, then after correcting the calculated position error by use of information of the position error, and comparing the error-corrected inspection image and reference image.

3. The inspection apparatus according to claim 1,
   wherein the detection optics includes means for selecting predetermined, polarized components of the scattered light.

4. The inspection apparatus according to claim 3,
   wherein the means for selecting predetermined, polarized components is a polarizing beam splitter.

5. The inspection apparatus according to claim 1,
wherein the detection optics includes an objective lens, a spatial filter, and an image-forming lens, further including
a first photosensor disposed on a surface upon which the scattered light is imaged by the image-forming lens, and
a second photosensor disposed spacedly from the first photosensor, upon the imaging surface of the scattered light.

6. The inspection apparatus according to claim 5,
wherein an attenuator is disposed between either the first photosensor or the second photosensor and the image-forming lens.

7. The inspection apparatus according to claim 5,
wherein the first photosensor is set to have a sensitivity that is different from that of the second photosensor.

8. An apparatus for inspecting a substrate surface, the apparatus comprising:
first illumination optics for irradiating the substrate surface linearly with a rectilinearly polarized beam of light from a first oblique direction;
second illumination optics for irradiating the substrate surface linearly with another rectilinearly polarized beam of light from a second oblique direction;
detection optics for acquiring images based on the beams of light scattered from the substrate surface irradiated with the beams from the first and second illumination optics; and
means for comparing an image selected as an inspection image from the plurality of substrate surface images that the detection optics has acquired, and another image selected from the plurality of substrate surface images as a reference image different from the inspection image to detect a defect;
wherein the first illumination optics and the second illumination optics each includes polarization control means for controlling a polarizing direction of the light according to a direction orthogonal to a lengthwise direction of patterns of the substrate, and the polarization control means inclines the polarized light α angle to an orthogonal direction to a incidence plane of the polarized light, in which $$\alpha = \tan^{-1}\left(\frac{\tan\phi}{\cos\theta}\right)$$

where α is azimuth angle at which rectilinearly polarized light enters, φ is rotation angle in x-y plane and θ is elevation angle; and
wherein the illumination optics is constructed to irradiate the substrate at an azimuth angle inclined through 15° to 75° to the scanning direction of the substrate.

9. The inspection apparatus according to claim 8,
wherein the defect detection means detects the defect by using the inspection image and the reference image and calculating a position error between the inspection image and the reference image, then after correcting the calculated position error by use of information of the position error, and comparing the error-corrected inspection image and reference image.

10. The inspection apparatus according to claim 8,
wherein the direction in which the light is polarized on the substrate surface by the first illumination optics is controlled to be substantially the same as the direction in which the light is polarized on the substrate surface by the second illumination optics.

11. The inspection apparatus according to claim 10,
wherein the detection optics detects scattered light substantially of the same polarized state in the lump via a plurality of photosensors arranged to gear up to illumination regions created by the first illumination optics and the second illumination optics.

12. The inspection apparatus according to claim 8,
wherein the direction in which the light is polarized on the substrate surface by the first illumination optics is controlled to be substantially orthogonal to the direction in which the light is polarized on the substrate surface by the second illumination optics.

13. The inspection apparatus according to claim 12,
wherein the detection optics detects scattered light of different polarized states in the lump via a plurality of photosensors arranged to gear up to illumination regions created by the first illumination optics and the second illumination optics.

14. The inspection apparatus according to claim 8,
wherein the light from the first illumination optics, and the light from the second illumination optics irradiate substantially the same place on the substrate surface at the same time.

15. The inspection apparatus according to claim 14,
wherein the detection optics includes means for selecting predetermined, polarized components of the scattered light.

16. The inspection apparatus according to claim 15,
wherein the means for selecting predetermined, polarized components is a polarizing beam splitter.

17. The inspection apparatus according to claim 8,
wherein the light from the first illumination optics, and the light from the second illumination optics irradiate substantially adjacent positions on the substrate surface.

18. The inspection apparatus according to claim 17,
wherein the detection optics includes an objective lens, a spatial filter, and an image-forming lens, further including
a first photosensor for acquiring an image created by a first beam of light scattered from the substrate surface, the first scattered light having originated from the light sent from the first illumination optics, and
a second photosensor for acquiring an image created by a second beam of light scattered from the substrate surface, the second scattered light having originated from the light sent from the second illumination optics.

19. The inspection apparatus according to claim 18, further comprising:
a polarizing film between the first photosensor and the image-forming lens and between the second photosensor and the image-forming lens.

* * * * *